United States Patent
Myung et al.

(10) Patent No.: US 10,561,315 B2
(45) Date of Patent: Feb. 18, 2020

(54) MODULAR ADAPTERS FOR MOBILE OPHTHALMOSCOPY

(71) Applicant: THE BOARD OF TRUSTEES OF THE LELAND STANFORD JUNIOR UNIVERSITY, Stanford, CA (US)

(72) Inventors: David Myung, San Jose, CA (US); Robert Tienhan Chang, Palo Alto, CA (US); Alexandre Jais, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/560,873

(22) PCT Filed: Mar. 25, 2016

(86) PCT No.: PCT/US2016/024265
§ 371 (c)(1),
(2) Date: Sep. 22, 2017

(87) PCT Pub. No.: WO2016/154558
PCT Pub. Date: Sep. 29, 2016

(65) Prior Publication Data
US 2018/0116509 A1 May 3, 2018

Related U.S. Application Data

(60) Provisional application No. 62/138,271, filed on Mar. 25, 2015.

(51) Int. Cl.
*A61B 3/14* (2006.01)
*A61B 3/12* (2006.01)
(Continued)

(52) U.S. Cl.
CPC .............. *A61B 3/14* (2013.01); *A61B 3/12* (2013.01); *H04M 1/026* (2013.01); *A61B 3/113* (2013.01); *G03B 17/563* (2013.01); *H04N 5/2254* (2013.01)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS

| 4,461,551 A | 7/1984 | Blaha |
| 4,586,892 A | 5/1986 | Ichizawa et al. |

(Continued)

FOREIGN PATENT DOCUMENTS

| CN | 103110401 A | 5/2013 |
| JP | 2004279733 A | 10/2004 |

(Continued)

OTHER PUBLICATIONS

Bastawrous; Smartphone fundoscopy; Ophthalmology; 119(2); pp. 432-433.e2; Feb. 2012.

(Continued)

*Primary Examiner* — Mohammed A Hasan
(74) *Attorney, Agent, or Firm* — Shay Glenn LLP

(57) ABSTRACT

Modular lens adapter system are provided for use with a hand held computer device having a camera for mobile ophthalmoscopy. The modular lens adapter systems include an anterior adapter and a posterior adapter configured to removably engage with a hand held computer device. The anterior adapter can include a variable intensity light source, a clamp, and a movable macro lens. The posterior adapter can include a hand held computer device mount, a lens mount, and a telescoping arm with a first end and a second end with the first end configured to removably engage with (Continued)

the mount and the second end configured to contact the lens mount. Methods are also provided for using the systems to obtain an image of an anterior portion of the patient's eye and a posterior portion of the patient's eye.

23 Claims, 19 Drawing Sheets

(51) Int. Cl.
*H04M 1/02* (2006.01)
*A61B 3/113* (2006.01)
*G03B 17/56* (2006.01)
*H04N 5/225* (2006.01)

(58) Field of Classification Search
USPC .......................................................... 351/206
See application file for complete search history.

(56) References Cited

U.S. PATENT DOCUMENTS

| | | | |
|---|---|---|---|
| 4,856,892 A | 8/1989 | Ben Tovim | |
| 6,766,041 B2 | 7/2004 | Golden et al. | |
| 6,889,006 B2 | 5/2005 | Kobayashi | |
| 7,806,528 B2 | 10/2010 | Bedell et al. | |
| 7,883,210 B2 | 2/2011 | Filar | |
| 8,253,787 B2 | 8/2012 | Yamamoto | |
| 8,454,166 B2 | 6/2013 | Fateh | |
| 8,511,820 B2 | 8/2013 | Trachtman | |
| 8,725,210 B2 | 5/2014 | Yang | |
| 8,760,569 B2 | 6/2014 | Yang | |
| 8,798,453 B2 | 8/2014 | Lawton | |
| 8,836,778 B2 | 9/2014 | Ignatovich et al. | |
| 8,862,183 B2 | 10/2014 | Kulas | |
| D717,856 S | 11/2014 | Slawson et al. | |
| 8,888,288 B2 | 11/2014 | Iravani et al. | |
| 8,905,543 B2 | 12/2014 | Davis | |
| 8,922,366 B1 | 12/2014 | Honoré et al. | |
| 9,019,420 B2 | 4/2015 | Hurst et al. | |
| 9,031,610 B2 | 5/2015 | Kulas | |
| 9,066,683 B2 | 6/2015 | Zhou | |
| 9,149,179 B2 | 10/2015 | Barnard et al. | |
| 9,215,977 B2 | 12/2015 | Bitran | |
| 9,706,918 B2 * | 7/2017 | Myung .................. | A61B 3/117 |
| 2004/0208343 A1 | 10/2004 | Golden et al. | |
| 2005/0200707 A1 | 9/2005 | Yogesan et al. | |
| 2005/0270484 A1 | 12/2005 | Maeda et al. | |
| 2007/0280677 A1 | 12/2007 | Drake et al. | |
| 2009/0062686 A1 | 3/2009 | Hyde et al. | |
| 2010/0328420 A1 | 12/2010 | Roman | |
| 2011/0085138 A1 | 4/2011 | Filar | |
| 2011/0299036 A1 | 12/2011 | Goldenholz | |
| 2012/0062840 A1 | 3/2012 | Ballou et al. | |
| 2012/0176689 A1 | 7/2012 | Brown | |
| 2012/0229617 A1 | 9/2012 | Yates et al. | |
| 2012/0320340 A1 | 12/2012 | Coleman | |
| 2013/0083185 A1 | 4/2013 | Coleman | |
| 2013/0150123 A1 | 6/2013 | Kulas | |
| 2013/0293840 A1 | 11/2013 | Bartels | |
| 2013/0300919 A1 | 11/2013 | Fletcher et al. | |
| 2014/0002792 A1 | 1/2014 | Filar | |
| 2014/0071547 A1 | 3/2014 | O'Neill et al. | |
| 2014/0078594 A1 | 3/2014 | Springer | |
| 2014/0085603 A1 | 3/2014 | Su et al. | |
| 2014/0114208 A1 | 4/2014 | Smith et al. | |
| 2014/0132932 A1 | 5/2014 | Jung | |
| 2014/0228668 A1 | 8/2014 | Wakizaka et al. | |
| 2014/0268053 A1 | 9/2014 | Fabian et al. | |
| 2014/0327753 A1 | 11/2014 | Prabhakar | |
| 2014/0327754 A1 | 11/2014 | Prabhakar | |
| 2014/0327755 A1 | 11/2014 | Prabhakar | |
| 2014/0350379 A1 | 11/2014 | Verdooner | |
| 2015/0002950 A1 | 1/2015 | O'Neill et al. | |
| 2015/0042873 A1 | 2/2015 | Hunt | |
| 2015/0045012 A1 | 2/2015 | Siminou | |
| 2015/0098060 A1 | 4/2015 | Zhou | |
| 2015/0103317 A1 | 4/2015 | Goldfain et al. | |
| 2015/0104087 A1 | 4/2015 | Katuwal et al. | |
| 2015/0223678 A1 | 8/2015 | Goldfain et al. | |
| 2015/0223686 A1 | 8/2015 | Wang | |
| 2015/0254524 A1 | 9/2015 | Dickrell et al. | |
| 2015/0257639 A1 | 9/2015 | Manquez Hatta et al. | |
| 2015/0313462 A1 | 11/2015 | Reis | |
| 2015/0320313 A1 | 11/2015 | Stamile et al. | |
| 2016/0015264 A1 | 1/2016 | Pankajakshan et al. | |
| 2016/0051142 A1 | 2/2016 | Howes | |
| 2016/0367135 A1 | 12/2016 | Myung et al. | |
| 2017/0280996 A1 | 10/2017 | Myung et al. | |

FOREIGN PATENT DOCUMENTS

| | | | |
|---|---|---|---|
| JP | 2006212102 A | 8/2006 | |
| JP | 2007520243 A | 7/2007 | |
| JP | 2008093118 A | 4/2008 | |
| JP | 2008295725 A | 12/2008 | |
| JP | 2013104986 A | 5/2013 | |
| JP | 2005524462 A | 8/2018 | |
| WO | WO 03/043363 A1 | 5/2003 | |
| WO | WO2007/069294 A1 | 6/2007 | |
| WO | WO2012/176960 A1 | 12/2012 | |
| WO | WO2014/181096 A1 | 11/2014 | |
| WO | WO2015/035229 A2 | 3/2015 | |
| WO | WO2015/054672 A1 | 4/2015 | |
| WO | WO2015071779 A1 | 5/2015 | |

OTHER PUBLICATIONS

Chakrabarti; Application of mobile technology in ophthalmology to meet the demands of low-resource settings; Journal of Mobile Technology in Medicine; 1(4S); pp. 1-3; Dec. 2012.
Chhablani et al.; Smartphones in ophthalmology; Indian J. Ophthalmol.; 60(2); pp. 127-131; Mar./Apr. 2012 (Author Manuscript).
Echanique et al.; Ocular Cellscope; University of California at Berkeley; Electrical engineering and computer sciences; 23 pages; retrieved from the internet (http://digitalassets.lib.berkeley.edu/techreports/ucb/text/EECS-2014-91.pdf); May 16, 2014.
Haddock et al.; Simple, inexpensive technique for high-quality smartphone fundus photography in human and animal eyes; Journal of Ophthalmology; 2013; pp. 1-5; published online Sep. 19, 2013.
Hester et al.; Smart Phoneography—how to take slit lamp photographs with an iphone; 12 pages; retrieved Jul. 30, 2015 from the Internet (http://eyewiki.aao.org/Smart_Phoneography_-_How_to_take_slit_lamp_photographs_with_an_iPhone).
Kim et al.; Smartphone photography safety; Ophthalmology; 119(10); pp. 220-2201; Oct. 2012.
Lord et al.; Novel uses of smartphones in ophthalmology; Ophthalmology; 117(6); pp. 1274-1274 e3; Jun. 2010.
Teichman et al.; From iphone to eyephone: a technique for photodocumentation; Can. J. Ophthalmol.; 46(3); pp. 284-286; Jun. 2011.
Apple Developer; Apple app store connect user guide; 4 pages; retrieved from the internet (https://developer.apple.com/support/app-store-connect/); on Dec. 12, 2018.
Digisight; Paxos scope: User manual; 23 pages; retrieved from the interent (https://www.digisight.net/fe/documents/scope_hw.pdf) on Dec. 27, 2018.
Gianchandani; IOS Dev—encrypting images and saving them in app sandbox; 2 pages; retrived Dec. 12, 2018 from the internet (http://highaltitudehacks.com/2013/09/26/ios-dev-encrypted-images-and-saving-them-in-app-sandbox/); Sep. 26, 2013.
Github; Nicklockwood/iCarousel: A simple, highly customisable, data-driven 3D carousel for iOS and Mac OS; 30 pages; retrieved from the interent (https://github.com/nicklockwood/iCarousel); on Dec. 12, 2018.
Github; Project-imas / encryted-core-data; 6 pages; retrieved from the internet (https://github.com/project-imas/encrypted-core-data); on Dec. 12, 2018.

(56) References Cited

OTHER PUBLICATIONS

Github; RNCryptor/RNCryptor; 7 pages; retrieved from the internet (https://github.com/RNCryptor/RNCryptor); on Dec. 12, 2018.
Wikipedia: Soap note; 6 pages; retrieved from the inerent (https://en.wikipedia.org/wiki/SOAP_note); on Dec. 12, 2018.
Muyng et al,; entitled "Modular lens adapters for mobile anterior and posterior segment ophthalmoscopy," filed Sep. 28, 2018.
Karandikar; U.S. Appl. No. 16/317,896 entitled "Systems and methods for capturing, annotating and sharing ophthalmic images obtained using a hand held computer," filed Jan. 15, 2019.
Myung et al.; U.S. Appl. No. 16/258,507 entitled "Adapter for retinal imaging using a hand held computer," filed Jan. 25, 2019.

* cited by examiner

MODULAR ADAPTERS FOR MOBILE OPHTHALMOSCOPY

CROSS REFERENCE TO RELATED APPLICATIONS

This application claims the benefit of U.S. Provisional Patent Application No. 62/138,271, filed Mar. 25, 2015, titled "MODULAR SMARTPHONE ADAPTERS FOR MOBILE OPHTHALMOSCOPY," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This invention relates generally to ophthalmoscopy. In particular, the invention relates to lens adapters for mobile ophthalmoscopy that can be used in a modular fashion with mobile imaging devices, like smartphones and tablet computers.

BACKGROUND

Over the past decade, ophthalmic imaging has moved rapidly from film to digital. However, most of today's gold standard digital fundus cameras, for example, are large, expensive tabletop medical devices only available in eye clinics. With the advent of the smartphone and ever improving built-in cameras rivaling point-and-shoot pocket digital cameras, eye care providers have the opportunity to capture high quality images anywhere using their existing lenses without the need for expensive equipment. Combined with ubiquitous fast wireless internet, cloud storage, smartphone-enabled electronic medical records, and encrypted messaging, a modern smartphone can now be instantly transformed into a low cost, portable, ophthalmic imaging camera. The present disclosure advances the art by providing a customizable adapter system or kit for mobile anterior and posterior segment ophthalmoscopy.

SUMMARY OF THE DISCLOSURE

The present invention relates generally to a modular adapter with an anterior adapter and a posterior adapter that can removably engaged with a hand held computer device having a camera.

In general, in one embodiment, a modular lens adapter system including an anterior adapter configured to removably engage with a hand held computer device having a camera, the anterior adapter includes a variable-intensity light source, a clamp configured to removably engaged with the hand held computer device, and a movable macro lens configured to move the macro lens from a first position in coaxial alignment with an optical axis of the hand held computer device camera to a second position outside of the optical axis of the camera, the macro lens configured to image an anterior portion of an eye; and a posterior adapter with a mount configured to removably engage with the hand held computer device by contacting opposing sides of the hand held computer device, the posterior adapter includes a lens mount and a telescoping arm with a first end and a second end, the first end configured to removably engage with the mount and the second end configured to contact the lens mount, wherein the lens mount is configured to removably mount a posterior segment ophthalmoscopy lens configured for indirect ophthalmoscopy.

This and other embodiments can include one or more of the following features. The lens mount can be configured to fold relative to the telescoping arm. The lens mount can include an opening in an outer diameter of the lens mount, the opening can be configured to accommodate a shaft portion of the telescoping arm when the lens mount is in a folded position. The lens mount can be configured to be folded to be parallel and flush with the telescoping arm. The anterior adapter can further include a macro lens hinge configured to move the macro lens from the first position to the second position. The anterior adapter can further include a macro lens engagement surface configured to secure the macro lens in the first position in coaxial alignment with the optical axis of the hand held computer device camera and prevent rotation of the macro lens about the macro lens hinge to a position outside of the first position. The modular lens adapter can further include a macro lens holder adapted to hold the macro lens, the macro lens holder can be engaged with the macro lens hinge, wherein the macro lens engagement surface can further include a complementary surface to the macro lens holder. The anterior adapter can further include a removable battery source adapted to power the variable intensity light source. The variable intensity light source can include a light emitting diode (LED). The anterior adapter can be configured to engage with the hand held computer device adapter at more than one position relative to the hand held computer device. The anterior adapter can be configured to engage with more than one brand of hand held computer device. The clamp of the anterior adapter can include a spring to secure the clamp and anterior adapter relative to the hand held computer device. The clamp of the anterior adapter can include a first surface and a second surface, the first surface and second surface movable relative to each other such that the first surface and second surface can be configured to apply a compressive force against the hand held computer device. The first surface and second surface can be configured to apply a compressive force to a plurality of different hand held computer device shapes. The mount of the posterior adapter can have a dominant axis with a length that can be adjusted to a plurality of different lengths. The mount can include a first hand held computer device contact surface and a second hand held computer device contact surface defining the dominant axis. The posterior adapter can further include a locking mechanism configured to hold the length of the dominant axis of the mount. The locking mechanism can further be configured to secure the telescoping arm relative to the mount. The telescoping arm can be configured to be movable and lockable along a portion of the dominant axis of the mount. The locking mechanism can include a thumb screw. The modular lens adapter can include an open optical pathway between the macro lens and the lens mount. The modular lens adapter can further include a patient face engagement surface adjacent the lens mount. The anterior adapter and posterior adapter can be configured to be placed in a pocket. The telescoping arm can position the lens mount from the mount in a range of 1 cm to 20 cm. The modular lens adapter can further include a light collimating element configured to be used with the variable intensity light source. The light collimating element can be movable from a position in an optical light path of the variable intensity light source and a second position outside of the optical light path of the variable intensity light source. The light collimating element can be removable from the anterior adapter. The modular lens adapter can further include a modular optical light guide adapted to guide an optical light path of the variable intensity light source to coincide with an optical axis of the macro lens and hand held computer device camera. The modular optical light guide can further include a system of mirrors. The modular optical light guide can further include a rhomboid prism. The rhomboid prism can include a first surface configured to reflect light from the variable intensity light source towards the optical pathway of the hand held computer device camera and a second surface configured to reflect light from the first surface to be substantially parallel to the optical pathway of the hand held computer device camera. The rhomboid prism can include a first surface configured to reflect light from the variable intensity light source towards the optical pathway of the hand held computer device camera and a second surface configured to reflect light from the first surface to substantially coincide with the optical pathway of the hand held computer device camera. The modular optical light guide can be configured to be removable from the anterior adapter. The modular optical light guide can be configured to be movable relative to the variable intensity light source between a position in line with the optical light path of the variable intensity light source and a second position outside of the optical light path of the variable intensity light source. The modular optical light guide can be configured for direct ophthalmoscopy with the anterior adapter. The hand held computer device can be a smartphone, tablet, or other flatscreen computer device. The modular lens adapter can further include a polarizing filter. The polarizing filter can be a linearly polarizing filter. The polarizing filter can be a circularly polarizing filter. The anterior and posterior adapters can be reversibly connected to each other to create a 3-point fixation to the hand held computer device.

In general, in one embodiment, a method of imaging an anterior portion of a patient's eye, the method including clamping an anterior adapter to a hand held computer device having a camera, the anterior adapter including a variable intensity light source, a clamp configured to engage with the hand held computer device, and a movable macro lens configured to move the macro lens from a first position in coaxial alignment with an optical axis of the camera to a second position outside of the optical axis of the camera, the macro lens configured to image an anterior portion of the patient's eye; moving the macro lens to be in coaxial alignment with the optical axis of the camera of the hand held computer device; moving the hand held computer device and anterior adapter to focus on the anterior portion of the patient's eye; and receiving an image of the anterior portion of the patient's eye with the camera of the hand held computer device.

This and other embodiments can include one or more of the following features. The method can further include adjusting the variable intensity light source to provide a desired level of light from the variable intensity light source to the anterior portion of the patient's eye. The method can further include lining up the optical axis of the camera with an optical axis of the anterior adapter prior to clamping the anterior adapter. The anterior adapter can be any of the anterior adapters. The method can further include securing the macro lens in the first position by rotating the macro lens about a macro lens hinge of the anterior adapter and engaging the macro lens with a macro lens engagement surface of the anterior adapter, the macro lens engagement surface configured to secure the macro lens in the first position in coaxial alignment with the optical axis of the hand held computer device camera and prevent rotation of the macro lens about the macro lens hinge to a position outside of the first position.

In general, in one embodiment, a method of imaging a posterior portion of a patient's eye, the method including securing a mount of a posterior adapter to a hand held computer device including a camera, the posterior adapter including a telescoping arm with a first end and a second end, the first end configured to removably engage with the mount and the second end configured to contact a lens mount configured to removably mount a posterior segment ophthalmoscopy lens configured for indirect ophthalmoscopy; adjusting the telescoping arm along an axis of the mount to coaxially line up the lens mount with an optical axis of the camera of the hand held computer device; engaging a lens configured for indirect ophthalmoscopy with the lens mount; moving the hand held computer device and the posterior adapter to focus on the posterior portion of the patient's eye; adjusting a length of the telescoping arm to focus the camera of the hand held computer device on an image of the posterior portion of the patient's eye in the lens configured for indirect ophthalmoscopy; and receiving an image of the posterior portion of the patient's eye with the camera of the hand held computer device.

This and other embodiments can include one or more of the following features. The method can further include securing the mount of the posterior adapter by adjusting a length of the axis of the mount to accommodate a dimension of the hand held computer device. The method can further include engaging a first hand held computer device contact surface and a second hand held computer device contact surface of the mount with the hand held computer device. The method can further include locking a length of the axis of the mount to secure the mount relative to the hand held computer device. The method can further include locking a position of the telescoping arm along the axis of the mount after adjusting the telescoping arm along the axis of the mount to coaxially line up the lens mount with the optical axis of the camera of the hand held computer device. The posterior adapter can be the lens adapter. The method can further include clamping an anterior adapter to the hand held computer device having the camera, the anterior adapter including: a variable intensity light source, a clamp configured to engage with the hand held computer device, and a movable macro lens configured to move the macro lens from a first position in coaxial alignment with an optical axis of the camera to a second position outside of the optical axis of the camera, the macro lens configured to image an anterior portion of the patient's eye. The method can further include adjusting the variable intensity light source to provide a desired level of light to the posterior portion of the patient's eye. The method can further include adjusting the variable intensity light source to provide a desired level of light to the anterior portion of the patient's eye. The method can further include moving the macro lens to be in coaxial alignment with the optical axis of the camera of the hand held computer device; moving the hand held computer device and anterior adapter to focus on the anterior portion of the patient's eye; and taking an image of the anterior portion of the patient's eye with the camera of the hand held computer device. The anterior adapter can further include a light collimating element and further include passing light from the variable intensity light source through the light collimating element to provide collimated light to the anterior portion or the posterior portion the patient's eye. The method can further include providing a movable modular optical light guide with the anterior adapter. The method can further include moving the modular optical light guide relative to the anterior adapter to a position in line with an optical light path of the variable intensity light source. The method can further include passing light from the variable-intensity light source through the optical light guide. The modular optical light guide can further include a rhomboid prism with a first surface and a second surface and further include reflecting light from the variable intensity light source off of the first surface towards the second surface and reflecting light from the first surface off of the second surface to be substantially parallel to the optical pathway of the hand held computer device camera. The modular optical light guide can further include a rhomboid prism with a first surface and a second surface and further include reflecting light from the variable intensity light source off of the first surface towards the second surface and reflecting light from the first surface off of the second surface to substantially coincide with the optical pathway of the hand held computer device camera. The method can further include using the modular optical light guide for direct ophthalmoscopy with the anterior adapter to obtain a direct ophthalmoscopy image of the patient's eye. The hand held computer device can be a smartphone, tablet, or other flatscreen computer device. The method can further include reversibly engaging the anterior adapter and the posterior adapter to form an interlocking connection between the anterior adapter and the posterior adapter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
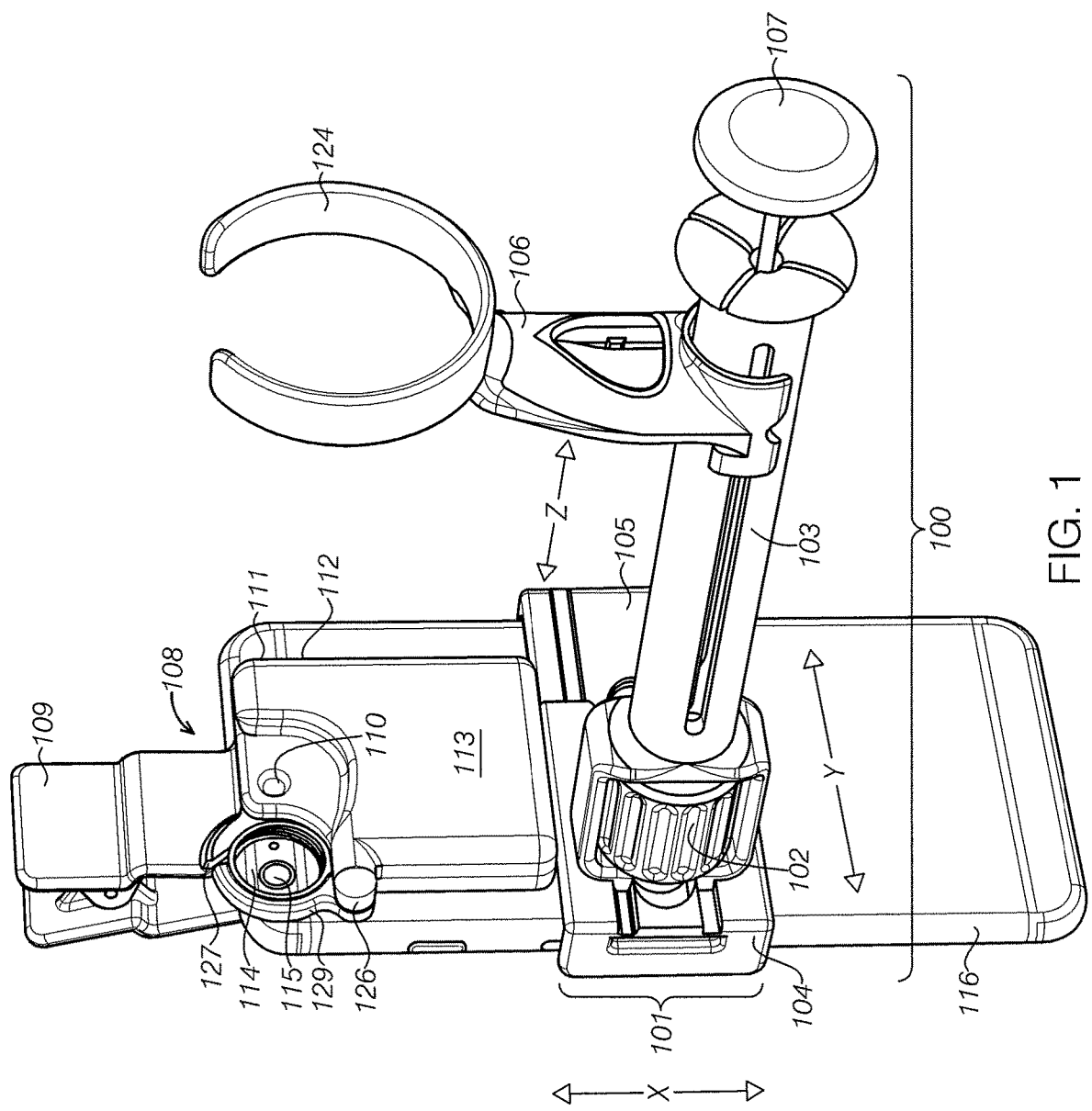
FIG. 1 shows a modular adapter including a posterior adapter and an anterior adapter engaged with a smartphone in accordance with some embodiments.

Improved modular lens adapters systems are described herein. The modular lens adapter systems include a posterior adapter and an anterior adapter. The modular lens adapter systems can be used with a variety of different hand held computer devices having different dimensions and different camera positions. The ability to quickly and easily engage the anterior adapter with hand held computer devices having different dimensions and camera positions greatly increases the utility of the system.

The modular adapter systems described herein can be combined with an inexpensive hand held computer device to form a low-cost and mobile ophthalmoscope that can be used to provide cost effective treatments to a variety of different patients. The present system allows, for example, the ability to treat patients in remote locations that do not have access to high quality eye care clinics.

A modular lens adapter system or kit is provided for mobile anterior and posterior segment ophthalmoscopy. Equipped with various lens adapter modules, respective lenses and a hand held computer device having a camera, a user is provided with tools for mobile ophthalmoscopy. The user can setup for various mobile ophthalmoscopy imaging applications like:

Posterior segment ophthalmoscopy using the ophthalmoscopy lens adapter with the hand held computer device having a camera with an internal variable intensity light source.

Posterior segment ophthalmoscopy using the ophthalmoscopy lens adapter with the hand held computer device and an external variable intensity light source.

Posterior segment ophthalmoscopy using the ophthalmoscopy lens adapter with the hand held computer device using the variable intensity light source of the anterior adapter with the macro lens out of the optical path of the hand held computer device and ophthalmoscopy lens.

Anterior segment ophthalmoscopy using the anterior adapter and a macro lens with the hand held computer device optionally using the variable intensity light source of the anterior adapter, where the ophthalmoscopy lens adapter is detached from the hand held computer device.

Anterior segment ophthalmoscopy using the anterior adapter with macro lens with the hand held computer device and its internal variable intensity light source, where the ophthalmoscopy lens adapter is detached from the hand held computer device.

With the embodiments of the adapters described herein, eye care practitioners can use their existing lenses to customize the modular lens adapter system in a cost-effective way, which allows for mobile and remote capture, viewing, and utilization of clinical images. The various modules are also adaptable to nearly any type of phone, tablet, or other hand held computer device having a camera regardless of its dimensions or presence of a protective case. The embodiments also address the reduced need for extra ophthalmic equipment, which is further important in enabling a broad base of users.

The modular lens adapter system can be used with hand held computer devices having different dimensions and camera locations. Examples of hand held computer devices include: mobile imaging devices, phones, smartphones (e.g. iPhone), personal digital assistant (PDA), tablet computer devices (e.g. iPad, iPod, etc.), flatscreen computer device, high definition webcam (wired and wireless), as well as digital cameras and video cameras with wireless and/or Bluetooth connectivity, all with at least a camera option for making still images and/or video. The exemplary embodiments are portrayed with an iPhone and different adapter modules, although these embodiments can be quickly adjusted to other smartphone brands and mobile devices of varying dimensions and camera locations.

The modular adapter systems include an anterior adapter and a posterior adapter that can be used separately or together.

The anterior adapter can include a variable intensity light source, a power source for the variable intensity light source, a clamp configured to removably engaged with the hand held computer device, and a movable macro lens. The anterior adapter can be configured to removably engage with the hand held computer device by engaging the clamp with the hand held computer device. The movable macro lens can move from a first position in coaxial alignment with an optical axis of the hand held computer device camera to a second position outside of the optical axis of the camera. In one example the macro lens can be moved between the first position and the second position by rotating the macro lens and/or macro lens holder about a macro lens hinge. A macro lens engagement surface can be used to secure the macro lens holder and macro lens in the first position. The macro lens can be used for imaging an anterior portion of the patient's eye and moved out of the optical pathway of the camera of the held computer device when using the posterior adapter to image the patient's eye.

The macro lens may be a commercially available macro lens manufactured specifically for smartphones. The macro lens may have a focal length ranging from about 1 cm to about 20 cm.

Preferably, the variable intensity light source is an LED light source with an adjustable intensity that can be adjusted with, for example, dial control. The control element for the LED intensity may be a dial, but could also be, but not limited to, a knob, a sliding switch, a haptic touch button, or a button.

The power source for the variable intensity light source can include a removable battery source adapted to power the variable intensity light source. In some embodiments the variable intensity light source comprises a light emitting diode (LED) or a plurality of LEDs.

The anterior adapter is designed to engage with a variety of different sizes and thicknesses of hand held computer devices. The anterior adapter is configured to engage with the hand held computer device adapter at more than one position relative to the hand held computer device such that the anterior adapter can be lined up with the optical axis of the camera of the hand held computer device. This allows the anterior adapter to engage with more than one brand of hand held computer device since different brands and models have different dimensions and unique camera locations. For the anterior adapter the back area (e.g. contacting the smartphone) is adapted to the hand held computer device.

In some embodiments the anterior adapter includes a clamp to secure itself relative to the hand held computer device. The clamp can include a spring to secure the clamp and anterior adapter relative to the hand held computer device. The clamp can include a first surface and a second surface with the first surface and second surface movable relative to each other such that the first surface and second surface can apply a compressive force against the hand held computer device.

The anterior adapter can be used with the hand held computer device to obtain an image of an anterior portion of the patient's eye using the macro lens. Methods for imaging the anterior portion of the eye can include clamping the anterior adapter to a hand held computer device having a camera, moving the macro lens to be in coaxial alignment with the optical axis of the camera of the hand held computer device, moving the hand held computer device and anterior adapter to focus on the anterior portion of the patient's eye, and receiving an image of the anterior portion of the patient's eye with the camera of the hand held computer device.

The user can line up the optical axis of the camera with the optical axis of the anterior adapter prior to clamping the anterior adapter. The clamp allows for quick and easy adjustment of the anterior adapter relative to the smartphone to line the optical axis of the camera with the optical axis of the anterior adapter and macro lens.

The variable intensity light source can be adjusted to provide the desired level of light from the variable intensity light source to the anterior portion of the patient's eye. Many hand held computer devices with light sources do not offer easy control of the light source and/or provide an easy way to provide lower levels of light suitable for directing at a patient's eye. The light sources on board the hand held computer devices are often too bright to shine into the patient's eye. The variable intensity light sources described herein can be quickly and easily adjusted to provide a low level of light that is sufficient to obtain an image of the eye while not being too bright to make the patient uncomfortable.

The posterior adapter can include a mount, telescoping arm, and a lens mount. The mount can be configured to removably engage with the hand held computer device by contacting opposing sides of the hand held computer device. The telescoping arm can have a first end and a second end. The first end can be configured to removably engage with the mount. The second end can be configured to contact the lens mount. The lens mount can be configured to removably mount a posterior segment ophthalmoscopy lens configured for indirect ophthalmoscopy.

The telescoping arm allows for adjustment of the working distance (adjusting the focal point) between the hand held computer device and an ophthalmoscopy lens mounted to ophthalmoscopy lens adapter via lens mount. In some embodiments the telescoping arm can position the lens mount from the mount in a range of 1 cm to 20 cm. Various other mechanisms could also work, such as folding or collapsing arm segments with joints and therefore the invention is not limited to telescoping segments. The objective of the telescopic arms or even the folding or collapsing arm segments is that the size can be minimized for easy storage. In one example with the same objective of minimizing space, the telescoping arms could also be separated from each other.

The lens mount can be sized to accommodate an ophthalmoscopy lens in the range of 10D to 90D, such as a 14D, 20D, 22D, 28D, 30D, 40D, or 54D, 60, 66, and 90D condensing lens for indirect ophthalmoscopy. The working distance between the lens mount and the hand held computer device can be about 5.75" in the case of an iPhone and a Volk Panretinal 2.2 lens, but will vary depending on the combination of hand held computer device camera, ophthalmoscopy lens power, and the subject being examined. For instance, for certain combinations of patients and lenses, the working distance can be reduced approximately 2 inches, or lengthened to approximately 10 inches. Ophthalmoscopy lenses can be easily mounted and removed from the inner diameter of the lens mount. In a preferred embodiment, the inner diameter of lens mount has a slightly undersized fit to allow gripping of the ophthalmoscopy lens for easy insertion and removal. In another preferred embodiment, it would be desirable to make the ring of lens mount more flexible to allow easy insertion and removal of the ophthalmoscopy lens. In other embodiments, a clamp mechanism can be used to hold the lens. The clamp could utilize a ratchet type mechanism, a spring mechanism, an adjustable belt, a vice, an elastic band, or screws that can be adjusted to hold the lens in place. In one example, it could be desirable that the ophthalmoscopy lens adapter be minimized in size so that it can be stored in a pocket of a garment, e.g. a pocket of a doctor's coat.

In some embodiments the lens mount is configured to fold relative to the telescoping arm. The lens mount can include an opening in an outer diameter of the lens mount. The lens mount opening can be sized to accommodate a shaft portion of the telescoping arm when the lens mount is in a folded position. In some embodiments the lens mount is configured to be folded to be parallel and flush with the telescoping arm.

The mount of the posterior adapter can accommodate hand held computer devices with various dimensions. The mount of the posterior adapter can define a dominant axis (e.g. y-axis in FIG. 1) with a length that can be adjusted to a plurality of different lengths. The mount can include a first hand held computer device contact surface and a second hand held computer device contact surface defining the dominant axis. In some embodiments the posterior adapter also includes a locking mechanism configured to hold the length of the dominant axis of the mount. The locking mechanism can also be configured to secure the telescoping arm relative to the mount. The telescoping arm can be moved along the dominant axis to the desired position and then locked into the desired position. In some embodiments the locking mechanism comprises a thumb screw.

Methods of using the posterior adapter to image a posterior portion of the patient's eye are also provided. The methods can include securing the mount of a posterior adapter to a hand held computer device, adjusting the telescoping arm along an axis of the mount to coaxially line up the lens mount with an optical axis of the camera of the hand held computer device, engaging a lens configured for indirect ophthalmoscopy with the lens mount, moving the hand held computer device and the posterior adapter to focus on the posterior portion of the patient's eye, adjusting a length of the telescoping arm to focus the camera of the hand held computer device on an image of the posterior portion of the patient's eye in the lens configured for indirect ophthalmoscopy, and receiving an image of the posterior portion of the patient's eye with the camera of the hand held computer device.

Securing the mount of the posterior adapter can include adjusting a length of the axis of the mount to accommodate a dimension of the hand held computer device. In one example securing the mount can include engaging a first hand held computer device contact surface and a second hand held computer device contact surface of the mount with the hand held computer device. The length of the axis of the mount can be locked after it has been sized to contact the hand held computer device to secure the mount and posterior adapter to the hand held computer device.

The lock can further be used to secure the position of the telescoping arm along the dominant axis of the mount after lining up the optical axis of the lens mount with the optical axis the camera of the hand held computer device. For example, by tightening the illustrated adjustable dial.

In some embodiments the modular lens adapter includes an open optical pathway between the macro lens and the lens mount.

The modular lens adapter can include an optional patient face engagement surface adjacent the lens mount.

The anterior and posterior adapters can be small and lightweight such that they can be placed in a pocket of the user.

In some embodiments the anterior adapter includes a light collimating element configured to be used with the variable intensity light source. The light collimating element can be movable from a position in an optical light path of the variable intensity light source and a second position outside of the optical light path of the variable intensity light source. In some embodiments the light collimating element is removable from the anterior adapter. The light collimating element can be used to modify a diffuse light, such as a diffuse light emitted by the variable intensity light source in some embodiments, into a collimated light. Examples of light collimating elements include lenses such as a spheroconvex lens or spherocylindrical lens, or masks of various geometries including slit, rectangle, square, or circles of varying diameter such that the emitted light takes on the shape of the lens or mask (e.g. a slit-shaped, rectangular, or circular beam of light). There may also be various filters such that the light emitted with cobalt-blue or red-free, for instance.

In some embodiments the adapter can also include a modular optical light guide. The modular optical light guide can be adapted to guide an optical light path of the variable intensity light source to coincide with an optical axis of the macro lens and hand held computer device camera. In some embodiments the modular optical light guide is configured for direct ophthalmoscopy with the anterior adapter. The modular optical light guide can be used with the anterior adapter for direct ophthalmoscopy to obtain a direct ophthalmoscopy image of the patient's eye with the hand held computer device. For example, in some embodiments the modular optical light guide enables direct ophthalmoscopy of the retina and optic nerve. It also makes the light more coincident with the visual axis of the hand held computer device to enable improved image capture during indirect ophthalmoscopy with the posterior adapter.

In some embodiments the modular optical light guide includes a rhomboid prism. In one example, the rhomboid prism can include a first surface configured to reflect light from the variable intensity light source towards the optical pathway of the hand held computer device camera and a second surface configured to reflect light from the first surface to be substantially parallel to the optical pathway of the hand held computer device camera. In one example, the rhomboid prism includes a first surface configured to reflect light from the variable intensity light source towards the optical pathway of the hand held computer device camera and a second surface configured to reflect light from the first surface to substantially coincide with the optical pathway of the hand held computer device camera. In some examples, the rhomboid prism has reflective or partially reflective (and thus partially transparent) surfaces. In other examples, the light guide comprises hollow paths configured with reflective and partially reflective surfaces to redirect light along a desired pathway and ultimately to run coaxially with the visual axis of the camera lens.

The modular optical light guide can be configured to be removable from the anterior adapter. In some embodiments the modular optical light guide is configured to be movable relative to the variable intensity light source. The modular optical light guide can be movable between a position in line with the optical light path of the variable intensity light source and a second position outside of the optical light path of the variable intensity light source. In some embodiments, this movement is facilitated by a hinge, a dial-mechanism (e.g. a carousel), or a sliding mechanism, or a combination thereof. In some embodiments, there are multiple modular optical light guides that provide light of various properties, shapes, and wavelengths. In some embodiments, the modular optical light guide(s) are combined with masks or filters as described above.

In some embodiments the adapter includes a polarizing filter for one of the lenses and/or for the light source. Examples of polarizing filters include a linear polarizing filter and a circularly polarizing filter.

FIG. 1 shows a modular adapter including a posterior adapter and an anterior adapter engaged with a smartphone in accordance with some embodiments. The posterior adapter 100 has a universal phone-mounting end 101 containing an adjustable dial 102 that locks the position of the shaft 103 in the x-y plane and the two brackets 104 and 105 also in the x-y plane so that the mount can grip devices of virtually any width. On the other end of the shaft is the lens mount 106 that is foldable so that the mounted lens 122 shown in FIG. 4 can fold down onto the shaft. The lens mount 106 is movable in the z-axis direction to accommodate different focal lengths of the lens being used and the refractive power and axial length of the eye being examined. The adapter also has an optional retractable face-rest element 107 that can be used to stabilize the adapter on a patient's face, or alternatively on a user's hand or thumb during image acquisition. The lens mount 106 includes an interior surface 124 configured to removably receive and secure a lens 122 for indirect ophthalmoscopy.

The anterior adapter 108 is comprised of a clamp or clip 109, a light source 110, potentiometer 111 that controls the intensity of the light source 110, a light switch 112, a battery pack (internal to 113), and movable macro lens (114). The movable macro lens 114 can rotate relative a macro lens hinge 126 between a first position (shown in FIG. 1) in coaxial alignment with an optical axis 120 of the hand held computer device camera to a second position outside of the optical axis of the camera (shown in FIG. 4).

The anterior adapter includes a macro lens holder 129 configured to hold the macro lens 114. The macro lens holder is engaged with the macro lens hinge 126 and can rotate about the macro lens hinge 126. The macro lens holder 129 is configured to engage with a macro lens engagement surface 127 of the anterior adapter 108. The engagement surface 127 is configured to secure the macro lens 114 and macro lens holder 129 in the first position in coaxial alignment with the optical axis of the hand held computer device camera. The macro lens engagement surface 127 can prevent rotation of the macro lens 114, and macro lens holder 129 about the macro lens hinge 126 to a position outside of the first position. Essentially, the macro lens engagement surface 127 can provide some friction to keep the macro lens 114 in place while the macro lens 114 is being used. When the user is finished with the macro lens 114 then they can push on the macro lens holder 129 to disengage the macro lens holder 129 from the macro lens engagement surface 127 to rotate the macro lens 114 and macro lens holder 129 about the macro lens hinge 126 to a position outside of the first position. In some embodiments the macro lens engagement surface 127 includes a complementary shaped surface to the macro lens holder 129. In some embodiments the macro lens engagement surface 127 can include a friction surface, snap fit connection, other locking structures, and/or other complementary shapes that can be used to secure the lens and hold it in the first position while the macro lens is in use.

The light source 110 can be positioned adjacent to the native camera lens 115 in order to provide near coaxial illumination with the visual/optical axis of the camera lens. The high plus power lens and optional light collimating element can converge the emitted light into a circular spot. The rhomboid prism and/or mirror system angles the emitted light so that it travels exactly co-axial with the visual axis of the camera lens. The polarizing filters screen out circularly, horizontally, or vertically polarized light to help reduce glare. The rhomboid prism and/or mirror system, by enabling co-axial light, in turn enables a direct ophthalmoscopic view of a patient's retina.

Figure 2:
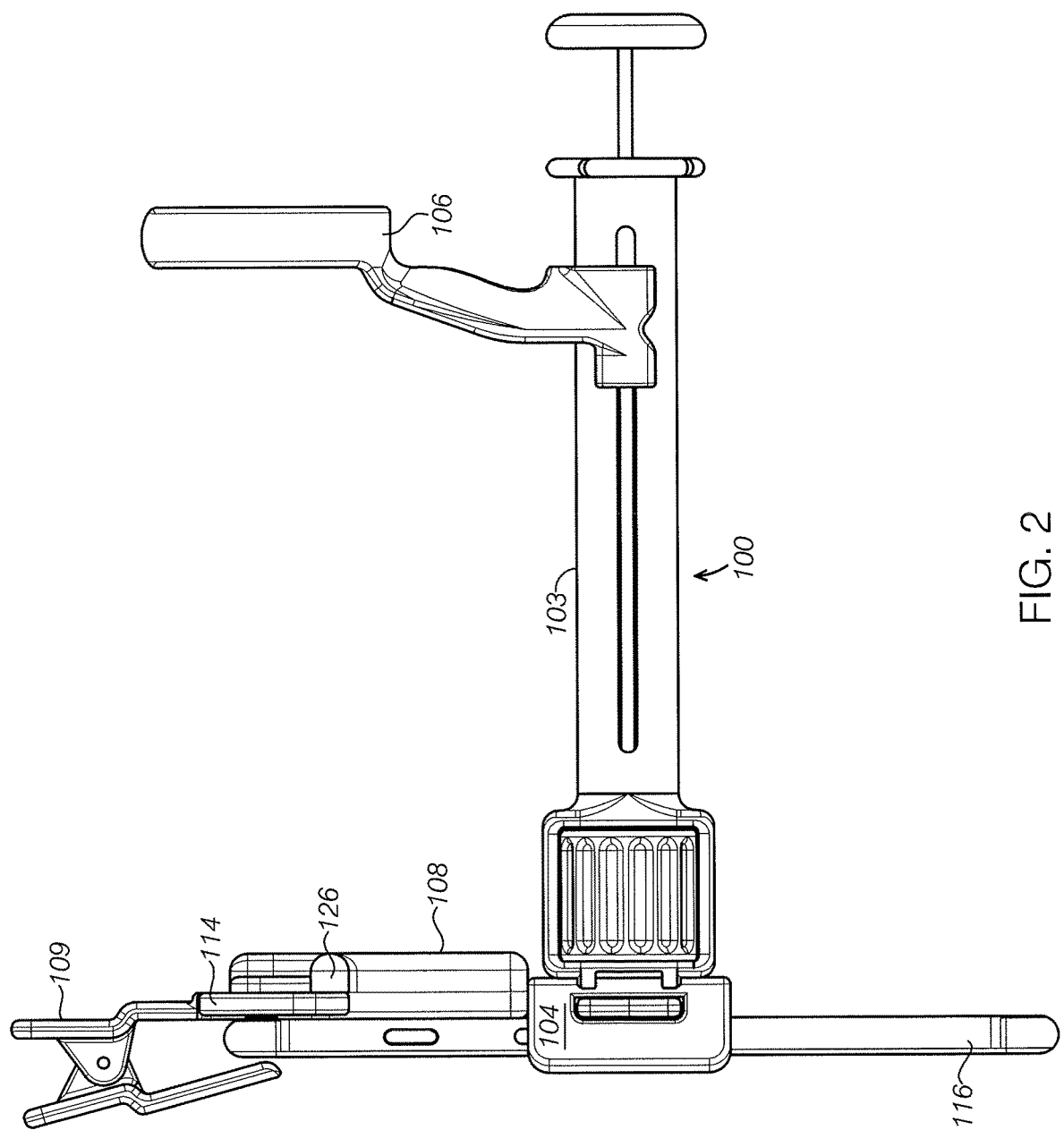
FIG. 2 shows a side view of a modular adapter including a posterior an adapter and anterior adapter engaged with a smartphone in accordance with some embodiments.

FIG. 2 shows a side view of a modular adapter including the posterior adapter 100 and anterior adapter 108 engaged with a smartphone 116. FIG. 2 shows the anterior adapter 108 secured to the smartphone 116 with clamp 109.

Figure 3:
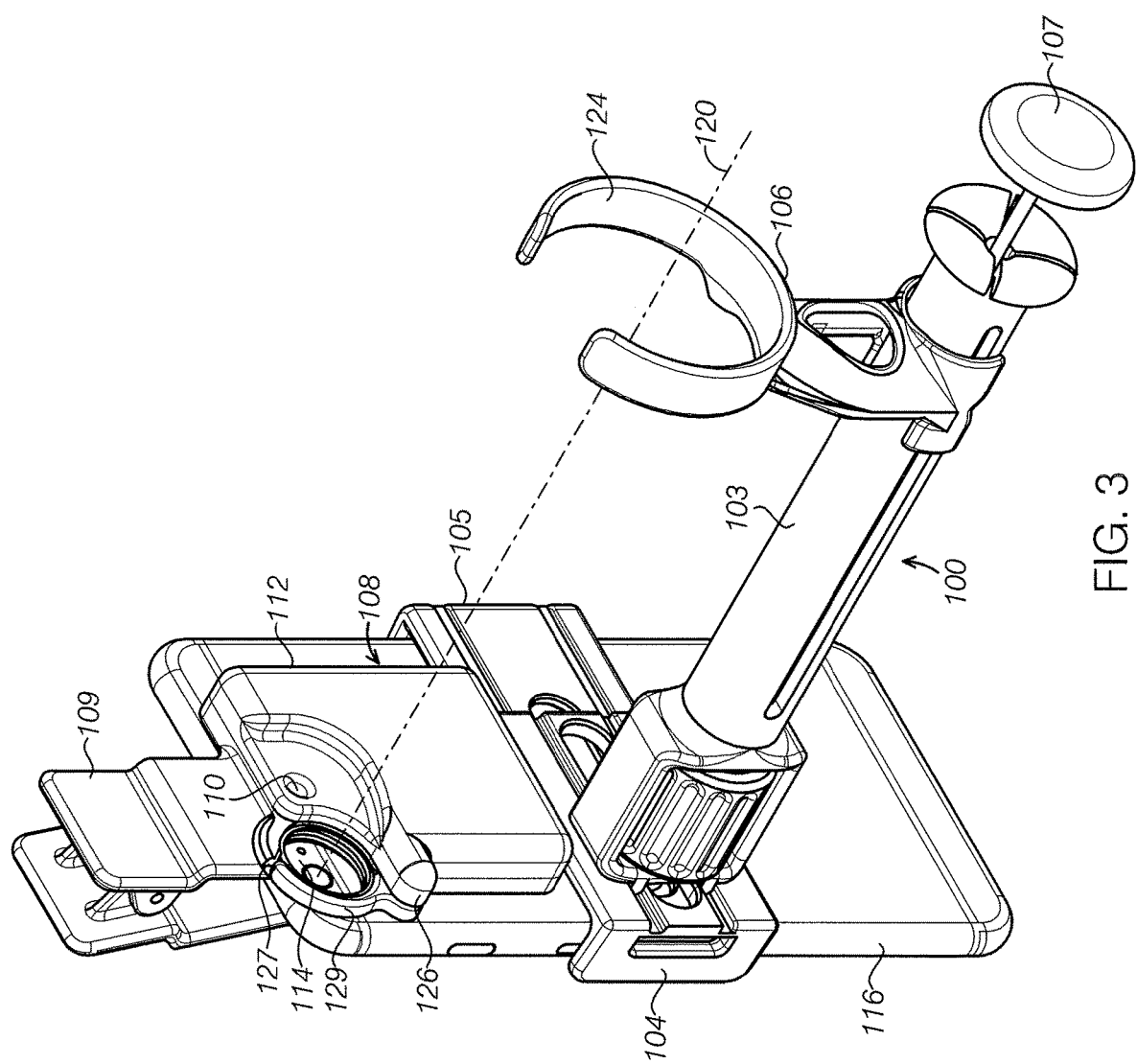
FIG. 3 shows a modular adapter including a posterior adapter and an anterior adapter engaged with a smartphone with the optical axis of the camera in line with an optical axis of the adapter in accordance with some embodiments.
Figure 4:
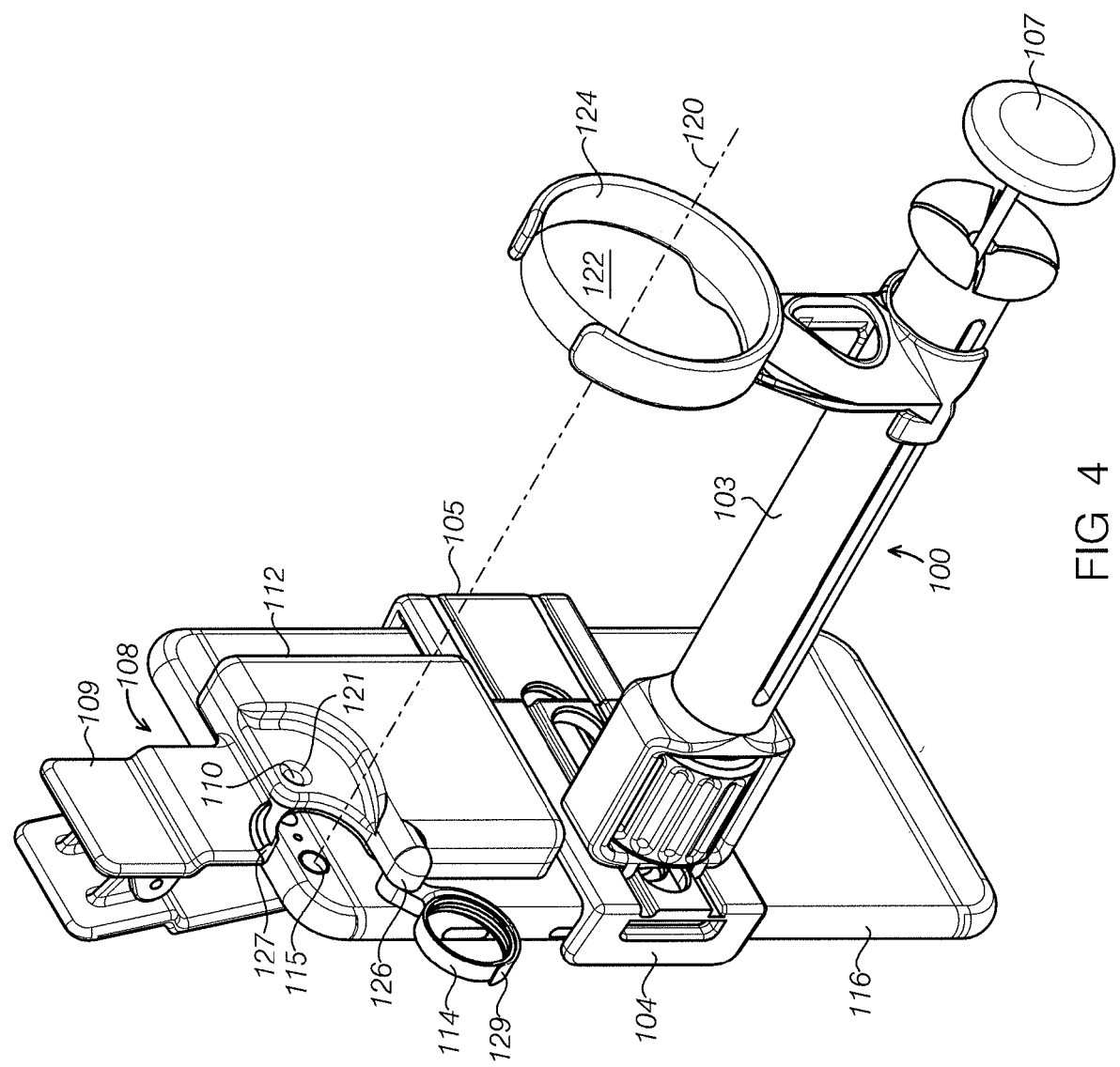
FIG. 4 shows a modular adapter including a posterior adapter and an anterior adapter engaged with a smartphone with a macro lens rotated away from the optical axis of the smartphone camera in accordance with some embodiments.

FIG. 3 shows an optical axis 120 of the modular adapter in line with the optical axis of the camera 115, macro lens 114, and lens mount 106. FIG. 4 shows a modular adapter with a macro lens 114 rotated away from the optical axis 120 of the camera. FIG. 4 shows the lens 122 and the optical axis 120 of the camera substantially coincidental with the optical axis of the lens 122 in the lens mount 106. FIG. 4 also illustrates an optional light-collimating element 121 adjacent to the light source 110.

Figure 5:
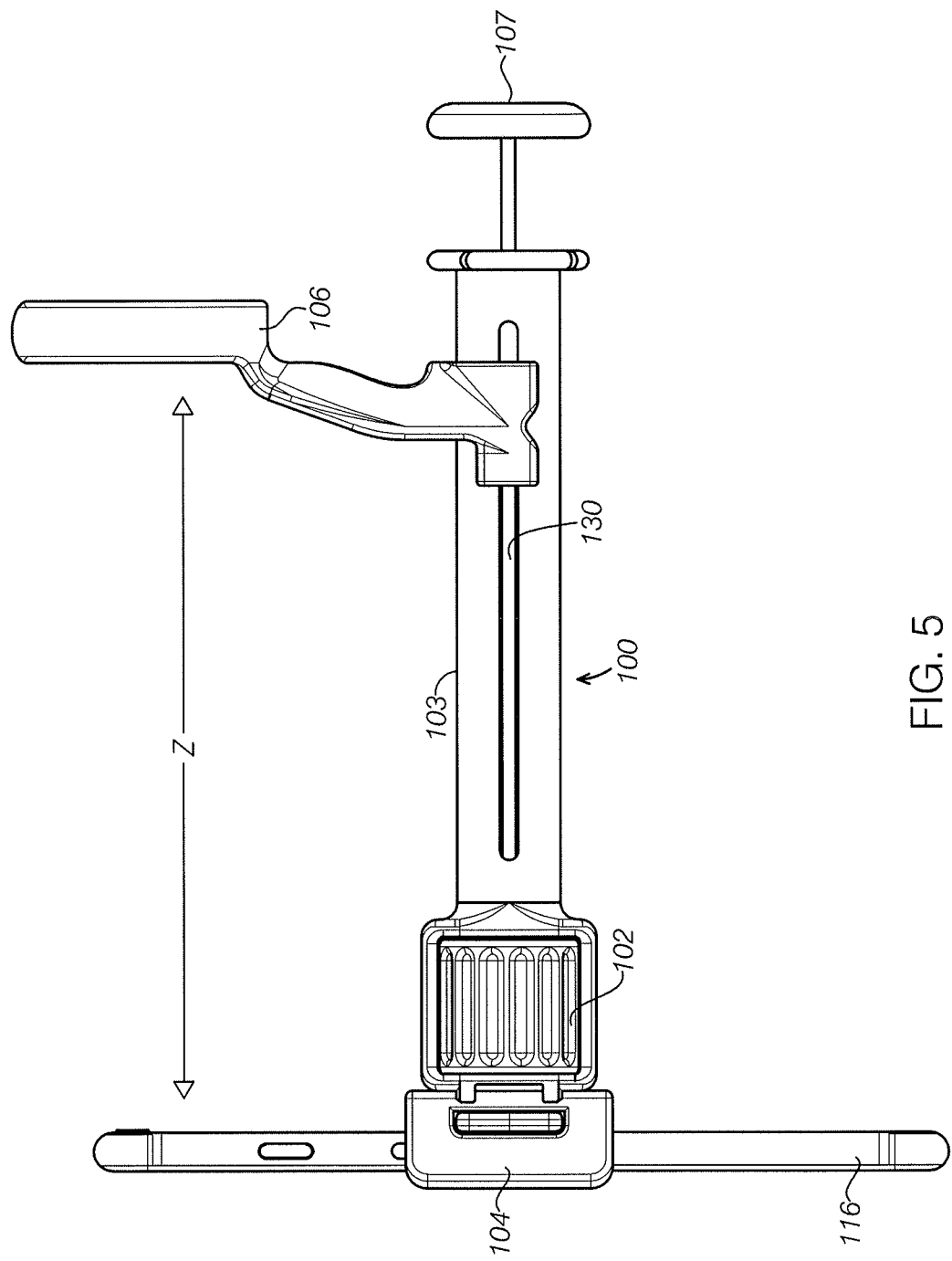
FIG. 5 shows a side view of a posterior adapter of a modular adapter engaged with a smartphone in accordance with some embodiments.

FIG. 5 shows a side view of a posterior adapter 100 engaged with a smartphone 100. The telescoping arm 103 includes a groove 130. The groove 130 allows the lens mount 106 to slide along the groove 130 so that the user can position the lens 122 and lens mount 106 to focus the image received by the camera 115 of the smartphone. The telescoping arm 103 can also change to vary the length of the telescoping arm 103 along the Z-axis. The lens mount 106 can also fold relative to the groove 130 to fold back along the telescoping arm 103 to make the device more compact and allow for it to fit within the pocket of the physician or user. For example the device can include a lens mount hinge between the telescoping arm 103 and the lens mount 106 to facilitate folding of the lens mount 106 relative to the telescoping arm 103.

Figure 6:
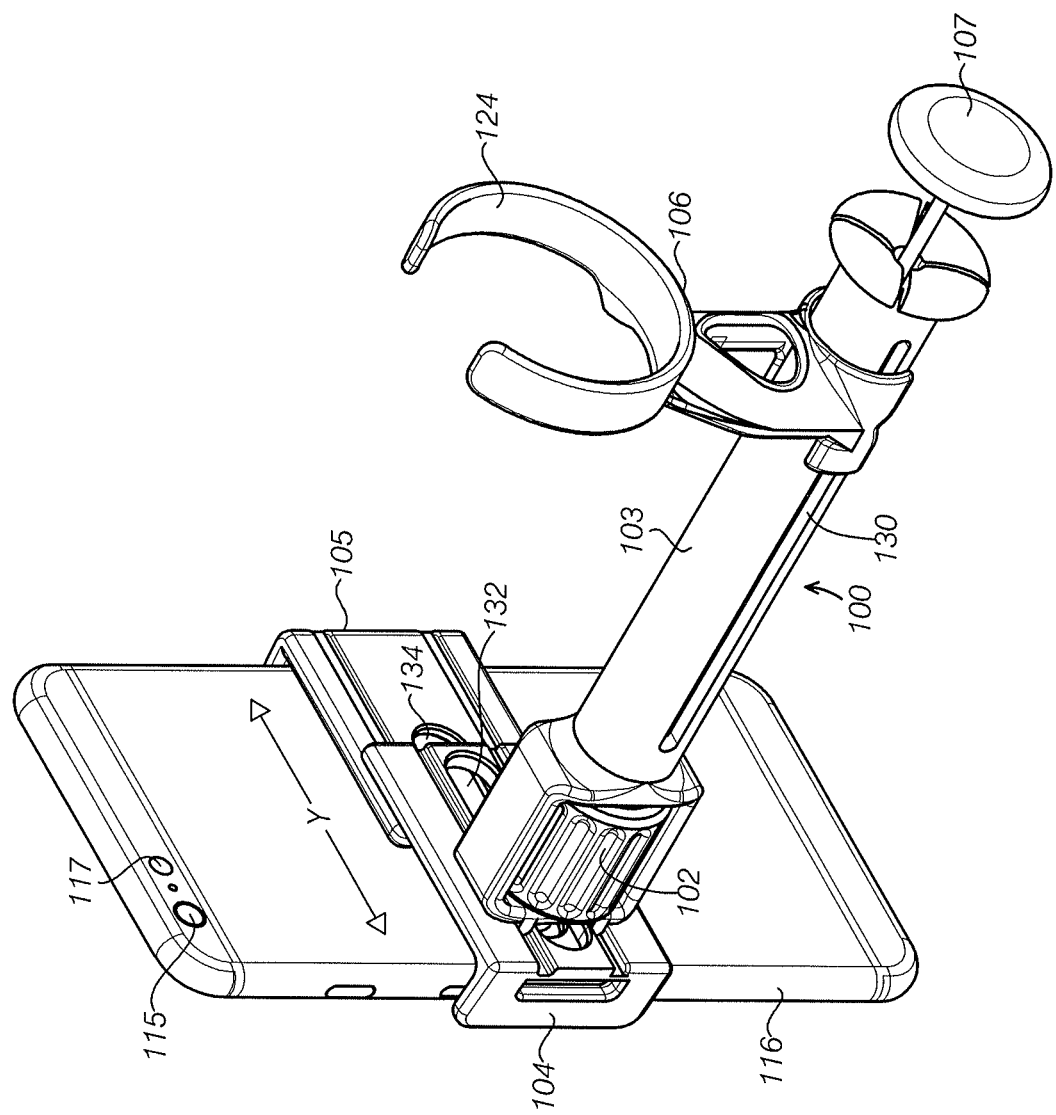
FIGS. 6-7 shows additional views of a posterior adapter of a modular adapter engaged with a smartphone in accordance with some embodiments.
Figure 7:
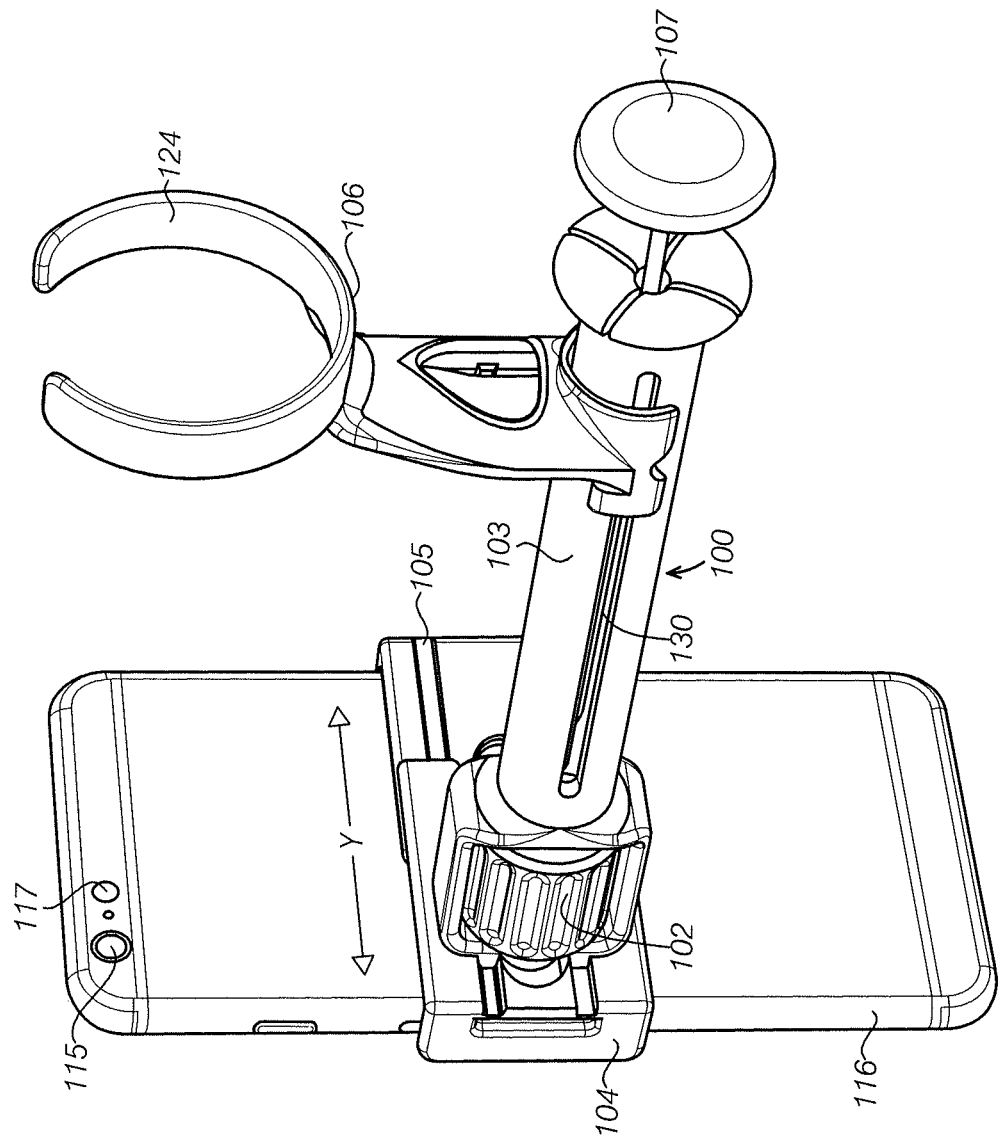

FIGS. 6-7 shows additional views of the posterior adapter 100 engaged with the smartphone 116. The brackets 104 and 105 can move relative to each other to increase or decrease the length of the brackets along the illustrated y-axis. This allows for the brackets 104, 105 to accommodate a hand held computer device having different widths. The bracket 104 includes an opening 132. The bracket 105 includes an opening 134. The openings 132, 134 allow the telescoping arm 103 to move along the axis of the openings, such as the illustrated y-axis. The adjustable dial 102 can be turned to secure the telescoping arm 103 relative to the brackets 104, 105 and bracket openings 132, 134. For example, the adjustable dial 102 can tighten a structure such that the dial engaged with and secures the brackets 104, 105 relative to each other and both brackets 104, 105 relative to the telescoping arm 103, thereby locking the posterior adapter 100 relative to the smartphone 116.

Figure 10:
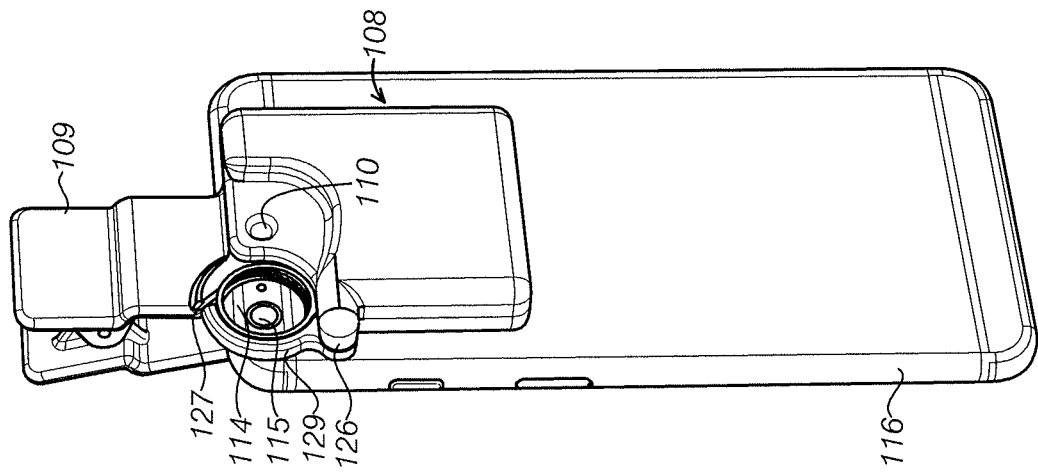
FIGS. 8-10 show various views of an anterior adapter engaged with a smartphone in accordance with some embodiments.
Figure 9:
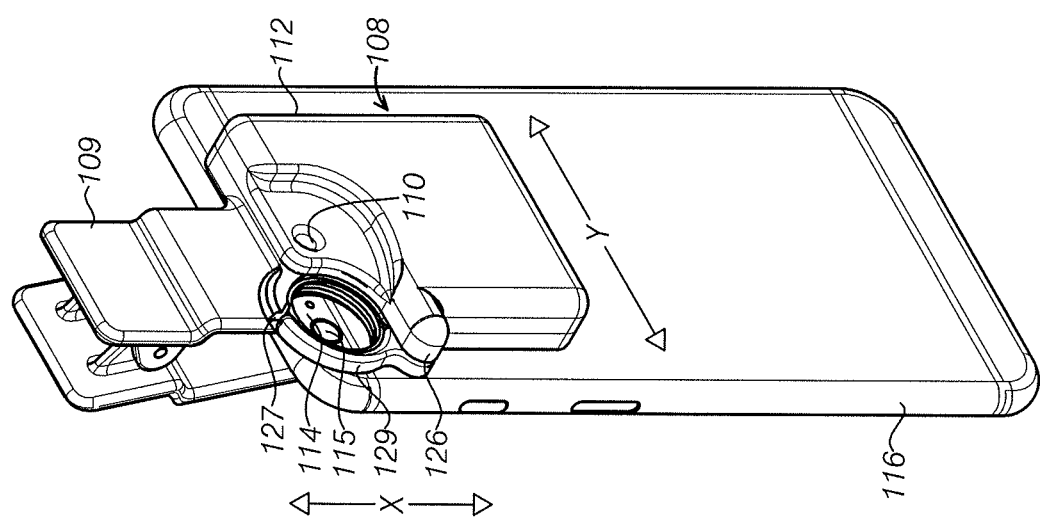
Figure 8:
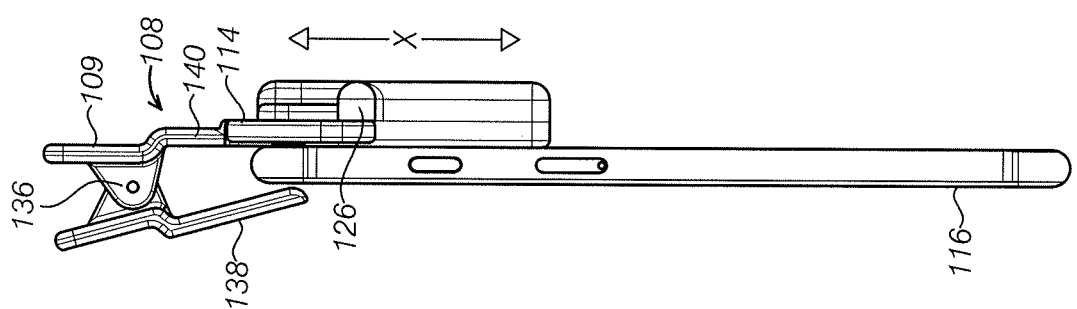

FIGS. 8-10 show various views of the anterior adapter 108 engaged with the smartphone 116. The anterior adapter 108 can be held in position relative to the smartphone 116 with the clamp 109. The illustrated clamp 109 includes a spring 136 that applies a compressive force with a first surface 138 of the clamp 109 and a second surface 140 of the clamp 109. The first surface 138 and second surface 140 of the clamp 109 secure the anterior adapter 108 relative to the smartphone 116. The clamp 109 can accommodate devices having many different widths and dimensions. The clamp 109 allows for the user to adjust the position of the anterior adapter 108 relative to the smartphone 116 and camera 115. The user can adjust the position of the anterior adapter 108 along the x-axis and y-axis to line up an optical axis of the camera 115 with the macro lens 114 and the optical axis of the macro lens (e.g. optical axis 120 shown in FIG. 3).

In some embodiments the lens used on the lens mount, for example lens mount 106 depicted in the Figures, may be optionally secured in place either through an interlocking, tightening, or adhesive mechanism. The mount itself may be removable, for instance in the case of different sized lens holders. The lens may be a conventional ophthalmoscopy lens made from glass, or a plastic lens; the lens preferably has an antireflective coating and a scratch-resistance coating such as a diamond coating. The lens may or may not be disposable. In some embodiments, the anterior and posterior adapters are reversibly joined or interlocked to create a stable, three-point fixation to the phone, and where the point of connection between the anterior and posterior adapters is modifiable.

In some embodiments an optional telescoping mechanism may be present on the shaft 103 enabling different working distances, to accommodate eyes with different axial lengths ranging from newborns with small eyes to long adult eyes, as well as different refractive errors ranging from hyperopic to myopic.

Examples of optional structures that can be used with the anterior adapter include an optional high plus power lens placed in front of the light source, and an optional rhomboid prism, optical light guide, mirrors, and polarizing filters that can be mounted over the light source and in front of the camera lens.

In some embodiments the LED may be emitted as a diffuse light, a collimated (spot) light, a slit, a square, or a rectangle. It may be white, blue, or red-free in color.

In some embodiments an enclosure may be present to connect the camera lens and LED to the lens within a cylindrical housing that is telescopable and/or retractable in order to position the lens at different working distances from the phone. In this setup, the shaft 103 may be optional, i.e. the enclosure serves as the holder for the distal lens. Additional lenses may be positioned between the distal lens and the camera to create a Galilean or Astronomical telescope system with different mounts of optical magnification.

Figure 11:
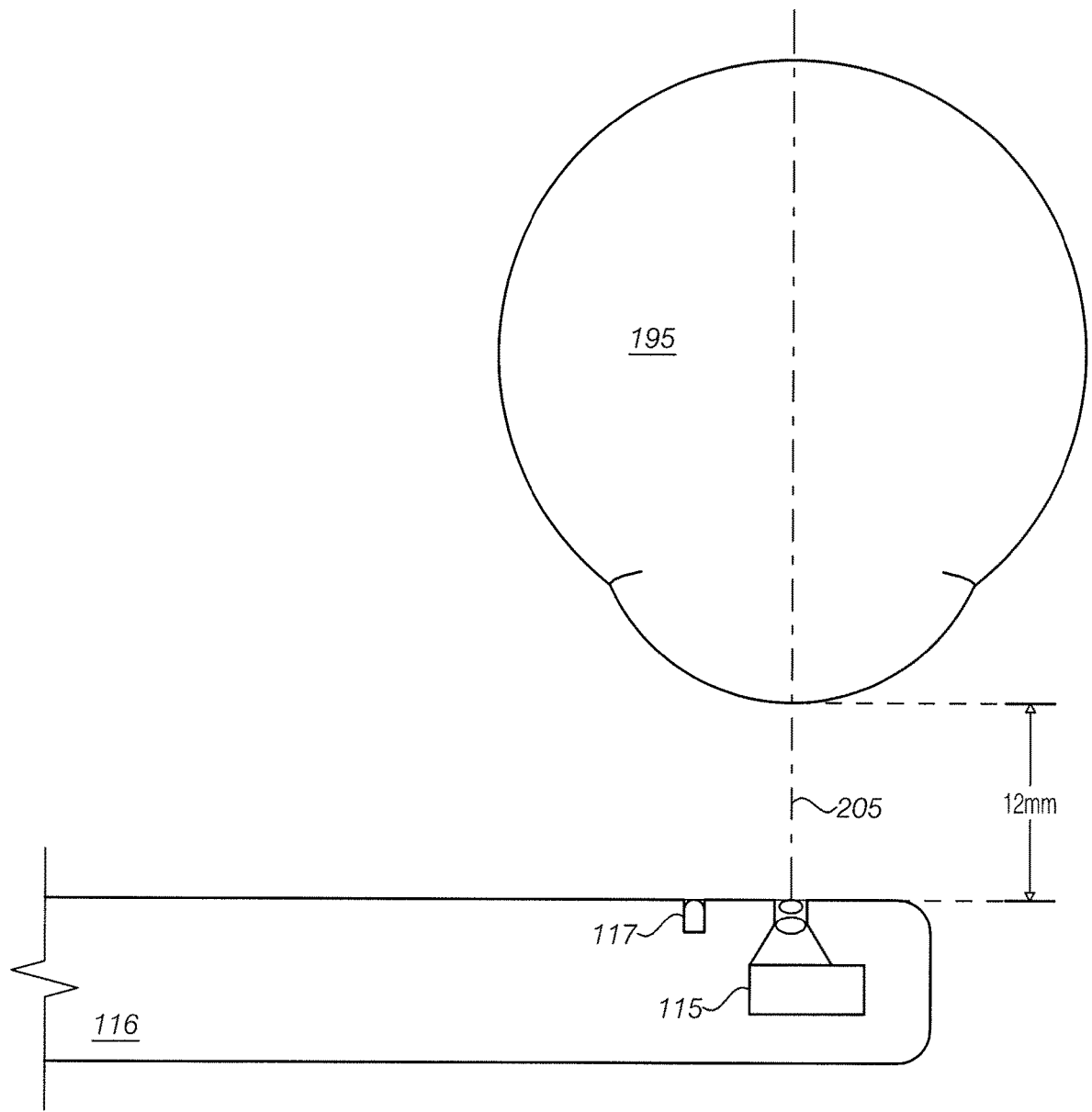
FIG. 11 is a schematic illustration of a smartphone with a light source and a camera imaging an eye.

FIG. 11 is a schematic illustration of a smartphone 116 with a light source 117 and a camera 115 imaging an eye 195 without the use of a modular adapter. The camera 115 has an optical path 205 directed at the eye 195. FIGS. 12-18 are schematic illustrations of various embodiments of adapters used with the smartphone 116 that modify a light path of a light source.

FIGS. 12-20 illustrate embodiments of optical light guides. The optical light guides can be used to direct the light from a light source on the hand held computer device and/or the anterior adapter (e.g. variable intensity light source) to be in line with the optical axis of a camera on the hand held computer device. The use of the optical light guide can allow for the imaging of the retina and optic nerve via direct ophthalmoscopy. For example, the light guide can shape the light path to facilitate providing light from the variable intensity light source to the optic nerve and retina along the axis of the camera of the hand held computer device. The camera of the hand held imaging device can then obtain a direct image of the retina and optic nerve that are illuminated by the light directed through the optical light guide. A red-free filtered illumination may be used in this case.

Figure 12:
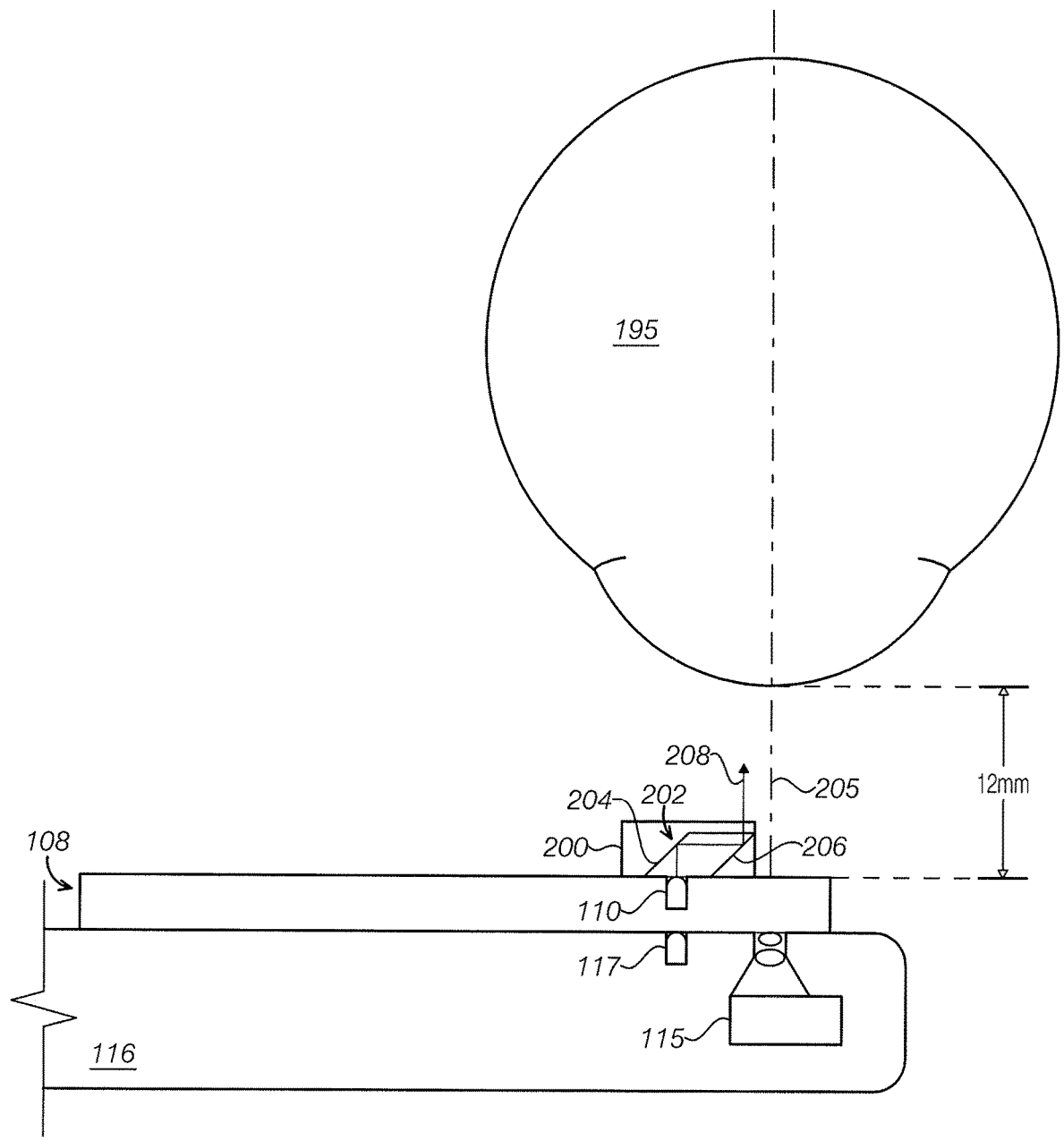
FIGS. 12-18 are schematic illustrations of various embodiments of adapters that modify a light path of a light source.

FIG. 12 illustrates an embodiment of an optical light guide 200 including a rhomboid prism 202 used with an anterior adapter 108 and a smartphone 116. The rhomboid prism 202 includes a first surface 204 and a second surface 206 for directing light emitted from the light source 110 of the anterior adapter 108 along an optical path 208. As shown in FIG. 12, the first surface 204 directs light emitted from the light source 110 along optical path 208 towards the second surface 206. The second surface 206 reflects the light reflected off of the first surface 204 along the optical path 208 towards the eye 195. The optical path 208 through the optical light guide 200 lines the optical path 208 exiting the optical light guide to be substantially parallel to the optical path 205 of the camera 115. In some embodiments the optical light guide 200 can line up the optical path 208 to substantially coincide with the optical path 205 of the camera 115. The optical light guide 200 can be used directly with the smartphone 116 and light source 117 or can be part of the anterior adapter 108 to direct the light emitted from the light source 110.

Figure 13:
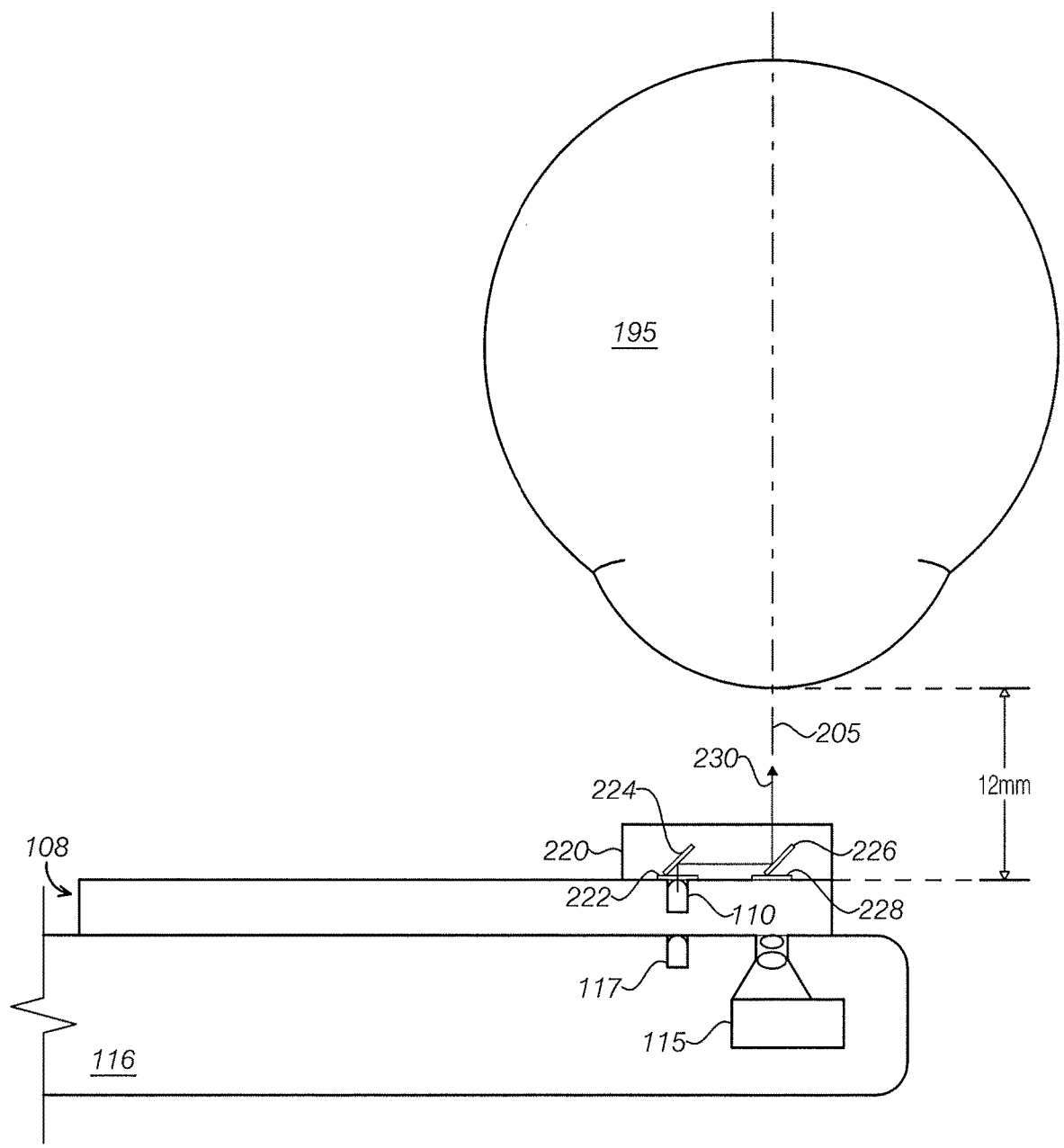

FIG. 13 illustrates an embodiment of an optical light guide 220 used with an anterior adapter 108 and a smartphone 116. The optical light guide 220 includes a polarizer Y 222, first mirror surface 224, polarizer X 228, and a second beamsplitter surface 226 for directing light emitted from the light source 110 of the anterior adapter 108 along an optical path 230. As shown in FIG. 13, the first mirror surface 224 directs light emitted from the light source 110 along optical path 230 towards the second beamsplitter surface 226. The second beamsplitter surface 226 reflects the light reflected off of the first mirror surface 224 along the optical path 230 towards the eye 195. The optical path 230 through the optical light guide 220 lines the optical path 230 exiting the optical light guide 220 to substantially coincide with the optical path 205 of the camera 115. The optical light guide 220 also passes the light from the light source 110 through the polarizer Y 222. The optical light guide 220 also adds a polarizer 228 to the optical path 205 of the camera 115. The optical light guide 220 can be used directly with the smartphone 116 and light source 117 or can be part of the anterior adapter 108 to direct light emitted from the light source 110.

Figure 14:
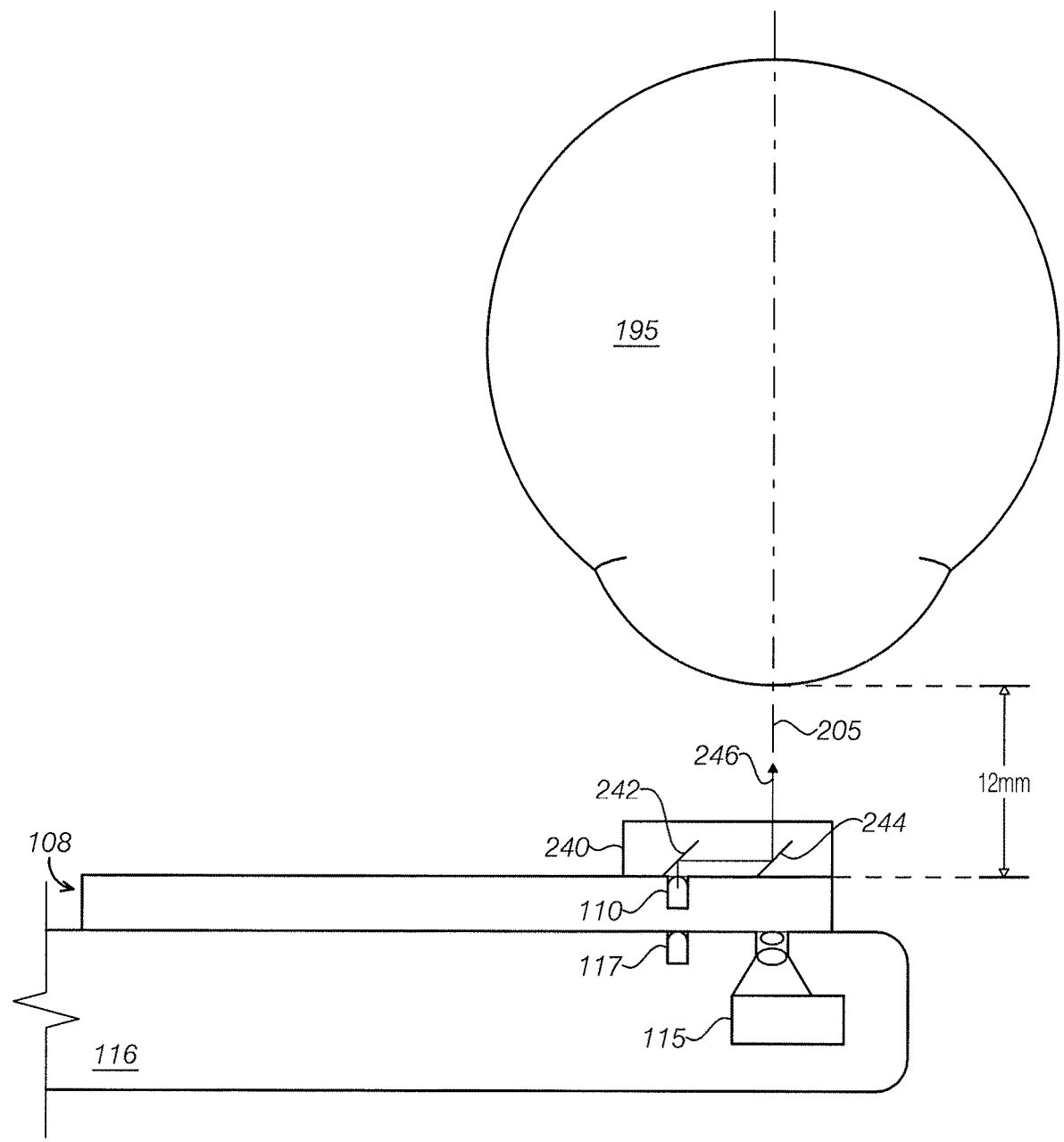

FIG. 14 illustrates an embodiment of an optical light guide 240 used with an anterior adapter 108 and a smartphone 116. The optical light guide 240 includes a first mirror surface 242 and a second beamsplitter surface 244 for directing light emitted from the light source 110 of the anterior adapter 108 along an optical path 246. As shown in FIG. 14, the first mirror surface 242 directs light emitted from the light source 110 along optical path 246 towards the second beamsplitter surface 244. The second beamsplitter surface 244 reflects the light reflected off of the first mirror surface 242 along the optical path 246 towards the eye 195. The optical path 246 through the optical light guide 240 lines the optical path 246 exiting the optical light guide 240 to substantially coincide with the optical path 205 of the camera 115. The optical light guide 240 can be used directly with the smartphone 116 and light source 117 or can be part of the anterior adapter 108 to direct light emitted from the light source 110.

Figure 15:
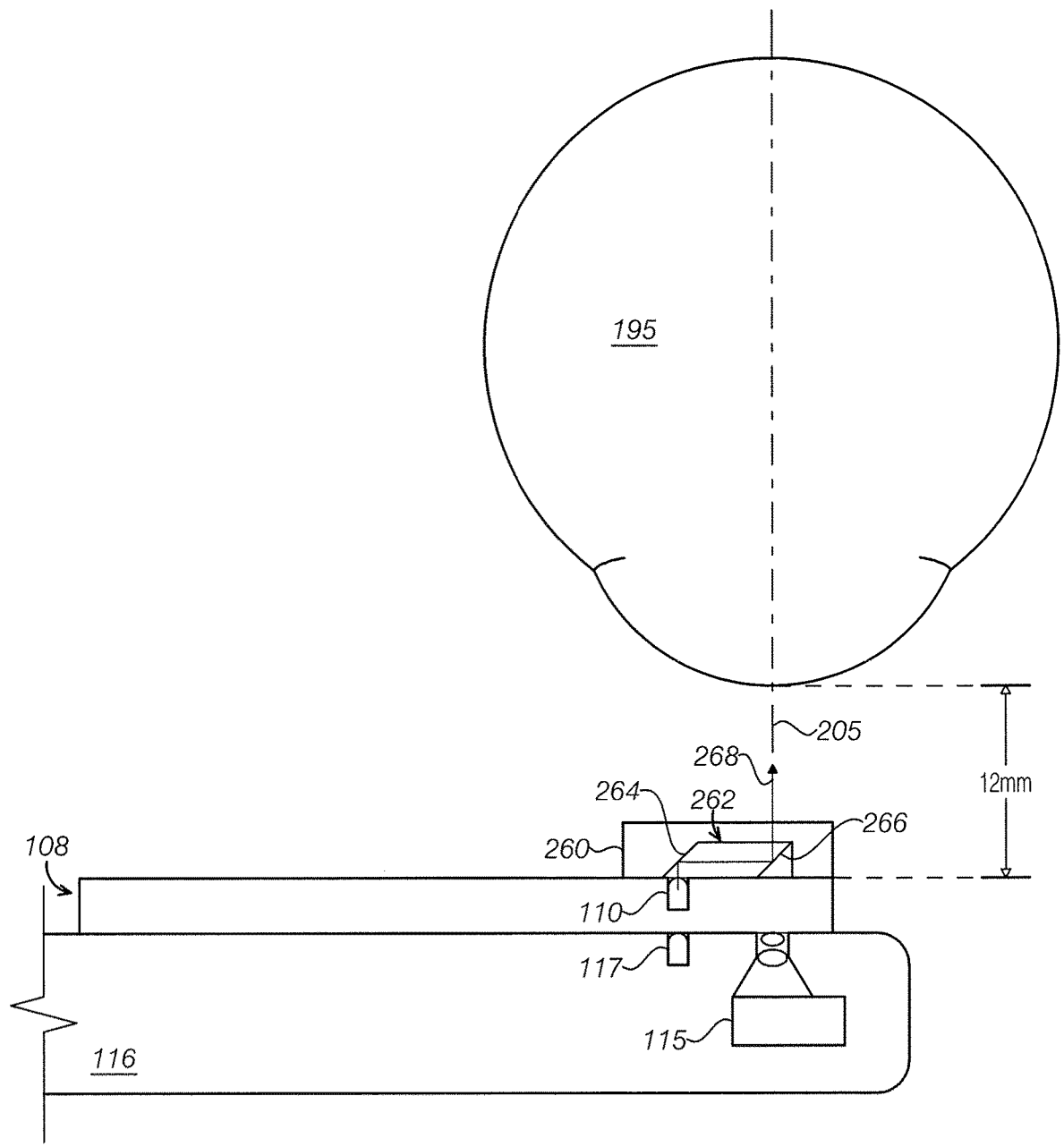

FIG. 15 illustrates an embodiment of an optical light guide 260 with a solid prism 262 used with an anterior adapter 108 and a smartphone 116. The solid prism 262 includes a first mirror surface 264 and a second surface with a beamsplitter coating 266 for directing light emitted from the light source 110 of the anterior adapter 108 along an optical path 268. As shown in FIG. 15, the first mirror surface 264 of the prism 262 directs light emitted from the light source 110 along optical path 268 towards the second surface with the beamsplitter coating 266. The second surface with the beamsplitter surface 266 reflects the light reflected off of the first mirror surface 264 along the optical path 268 towards the eye 195. The optical path 268 through the optical light guide 260 lines the optical path 268 exiting the optical light guide 260 to substantially coincide with the optical path 205 of the camera 115. The optical light guide 260 can be used directly with the smartphone 116 and light source 117 or can be part of the anterior adapter 108 to direct light emitted from the light source 110.

Figure 16:
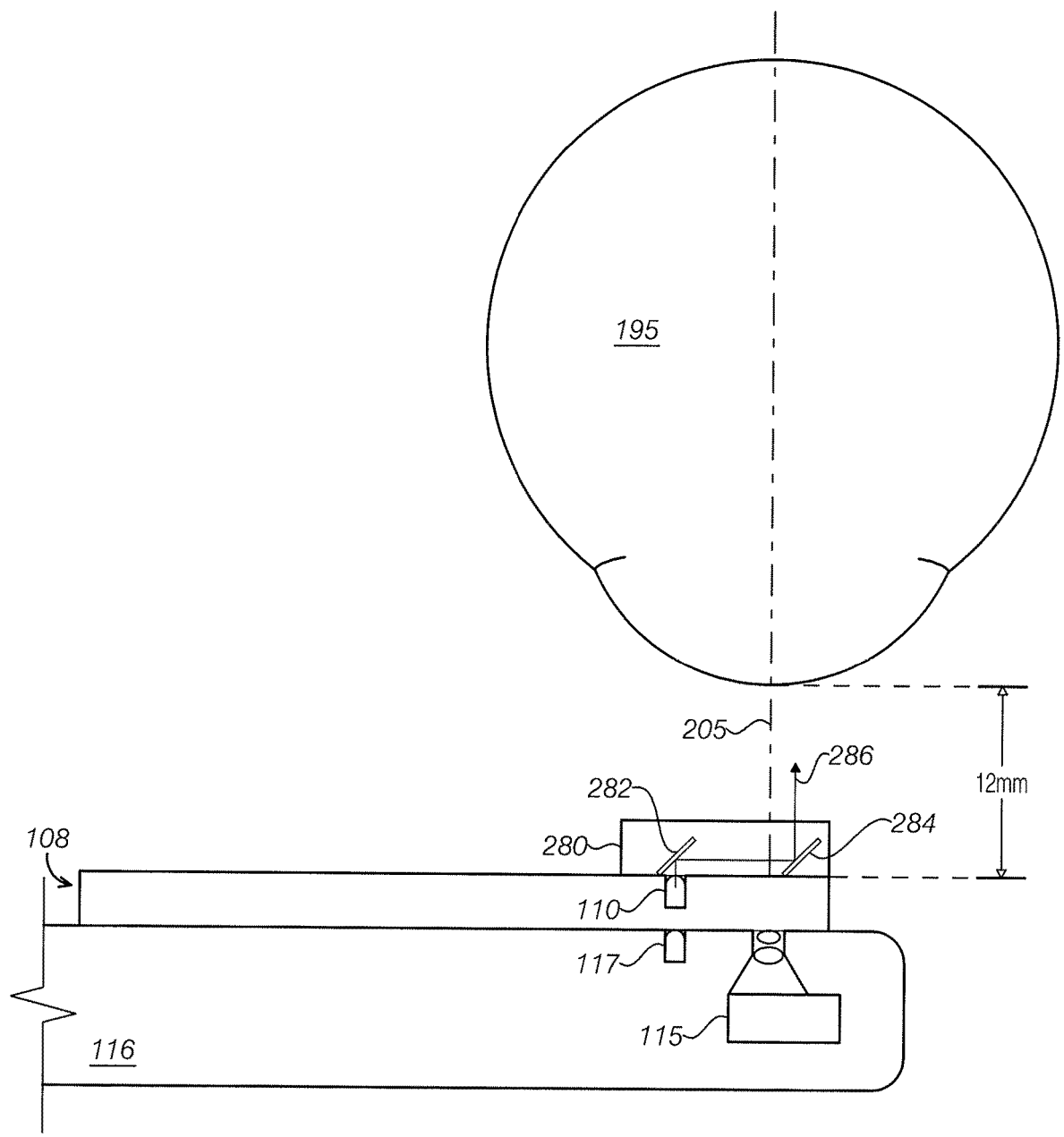

FIG. 16 illustrates an embodiment of an optical light guide 280 used with an anterior adapter 108 and a smartphone 116. The optical light guide 280 includes a first mirror surface 282 and a second mirror surface 284 for directing light emitted from the light source 110 of the anterior adapter 108 along an optical path 286. As shown in FIG. 16, the first mirror surface 282 directs light emitted from the light source 110 along optical path 286 towards the second mirror surface 284. The second mirror surface 284 reflects the light reflected off of the first mirror surface 282 along the optical path 286 towards the eye 195. The optical path 286 through the optical light guide 280 lines the optical path 286 exiting the optical light guide 280 to be offset from but substantially parallel with the optical path 205 of the camera 115. The optical light guide 280 can be used directly with the smartphone 116 and light source 117 or can be part of the anterior adapter 108 to direct light emitted from the light source 110.

Figure 17:
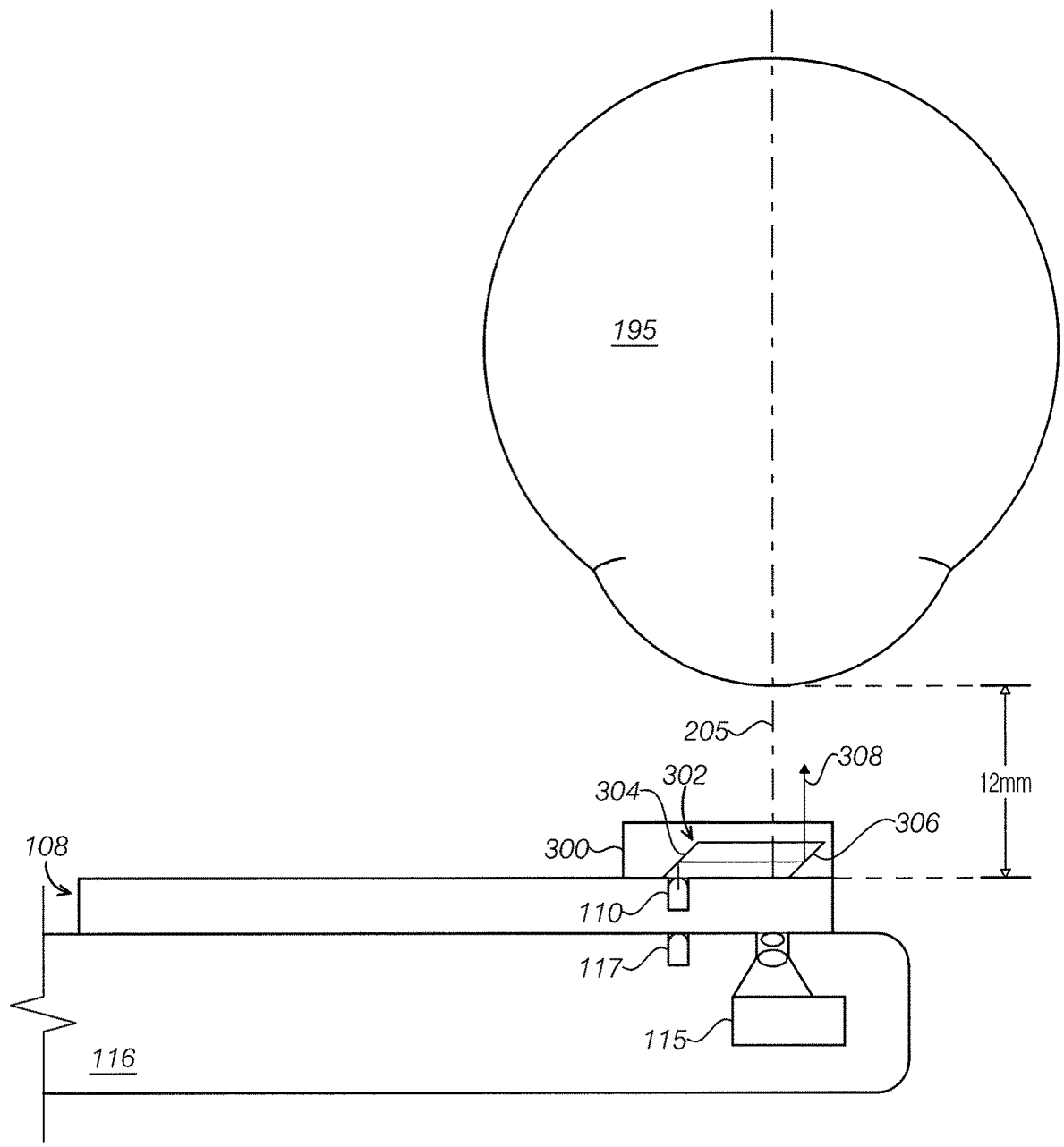

FIG. 17 illustrates an embodiment of an optical light guide 300 with a prism 302 used with an anterior adapter 108 and a smartphone 116. The prism 302 includes a first surface 304 and a second surface 306 for directing light emitted from the light source 110 of the anterior adapter 108 along an optical path 308. As shown in FIG. 17, the first surface 302 directs light emitted from the light source 110 along optical path 308 towards the second surface 306. The second surface 306 reflects the light reflected off of the first surface 304 along the optical path 308 towards the eye 195. The optical path 308 through the optical light guide 300 lines the optical path 308 exiting the optical light guide 300 to be offset from but substantially parallel with the optical path 205 of the camera 115. The optical path 205 of the camera 115 passes through the optical light guide 300 and prism 302 in FIG. 17. The optical light guide 308 can be used directly with the smartphone 116 and light source 117 or can be part of the anterior adapter 108 to direct light emitted from the light source 110.

Figure 18:
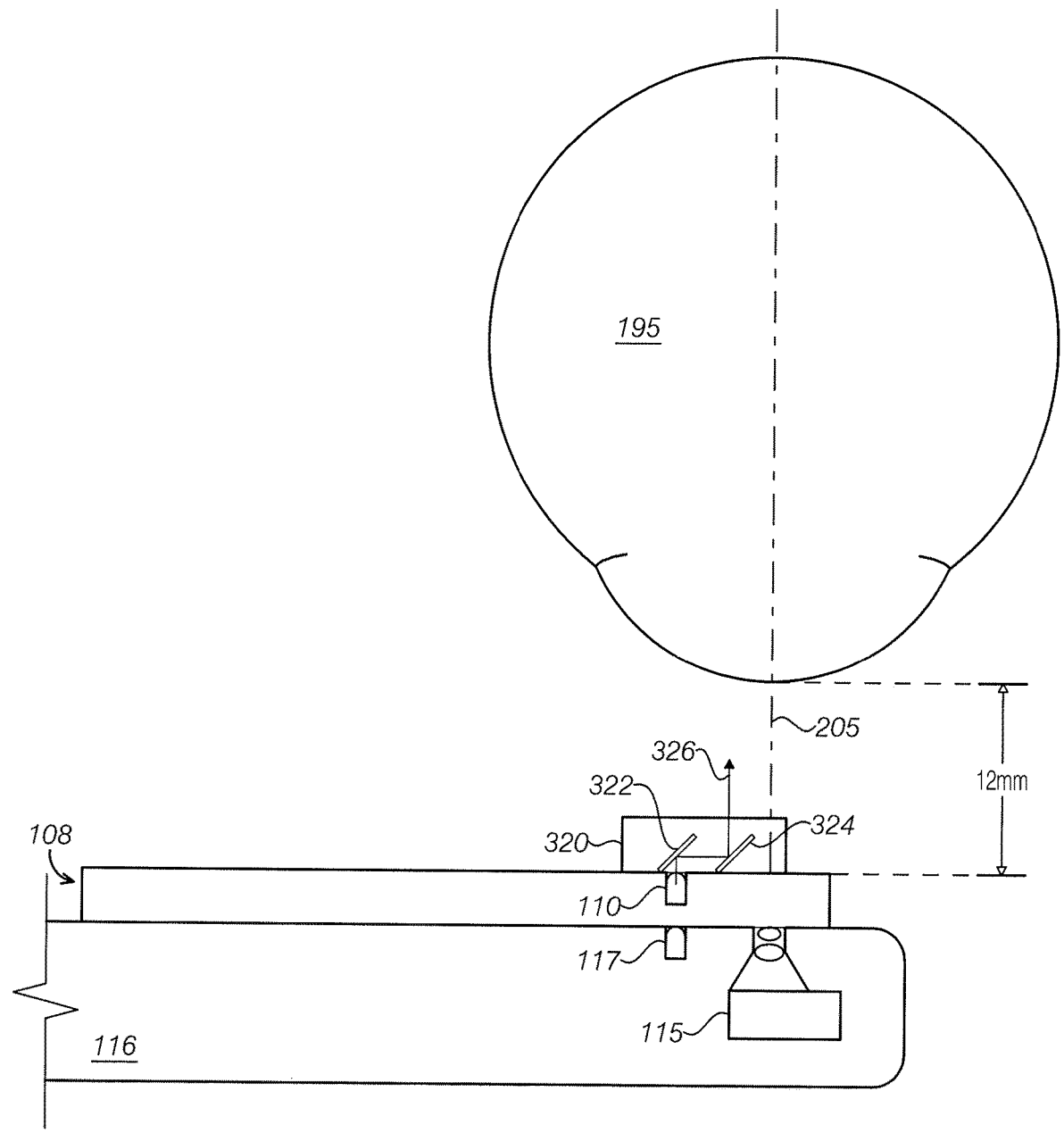

FIG. 18 illustrates an embodiment of an optical light guide 320 used with an anterior adapter 108 and a smartphone 116. The optical light guide 320 includes a first mirror surface 322 and a second mirror surface 324 for directing light emitted from the light source 110 of the anterior adapter 108 along an optical path 326. As shown in FIG. 18, the first mirror surface 322 directs light emitted from the light source 110 along optical path 326 towards the second mirror surface 324. The second mirror surface 324 reflects the light reflected off of the first mirror surface 322 along the optical path 326 towards the eye 195. The optical path 326 through the optical light guide 320 lines the optical path 326 exiting the optical light guide 320 to be offset from but substantially parallel with the optical path 205 of the camera 115. The optical light guide 320 can be used directly with the smartphone 116 and light source 117 or can be part of the anterior adapter 108 to direct light emitted from the light source 110.

Figure 19A:
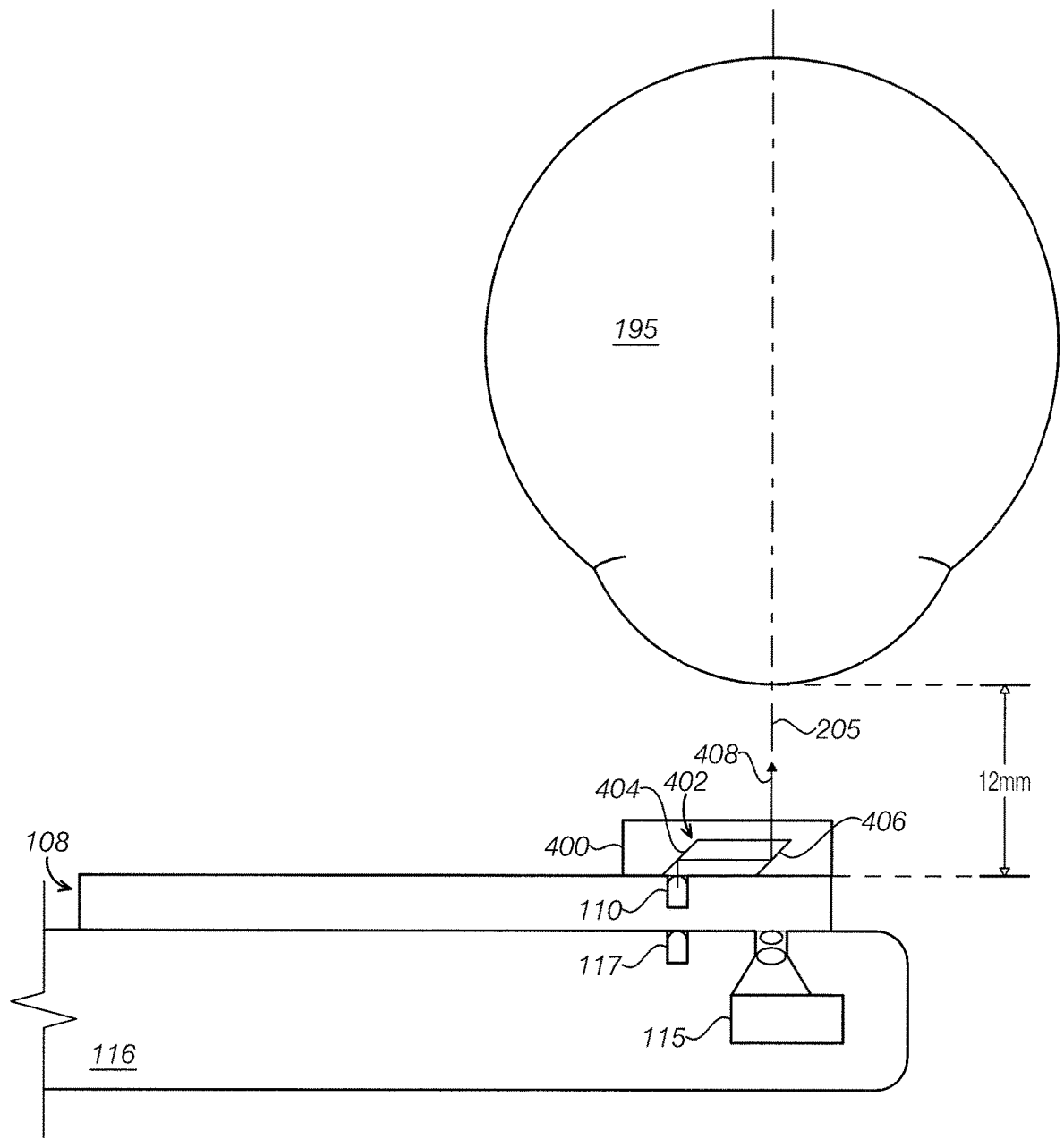
FIG. 19A is a schematic illustration of an adapter modifying a light path of a light source in accordance with some embodiments.
Figure 19B:
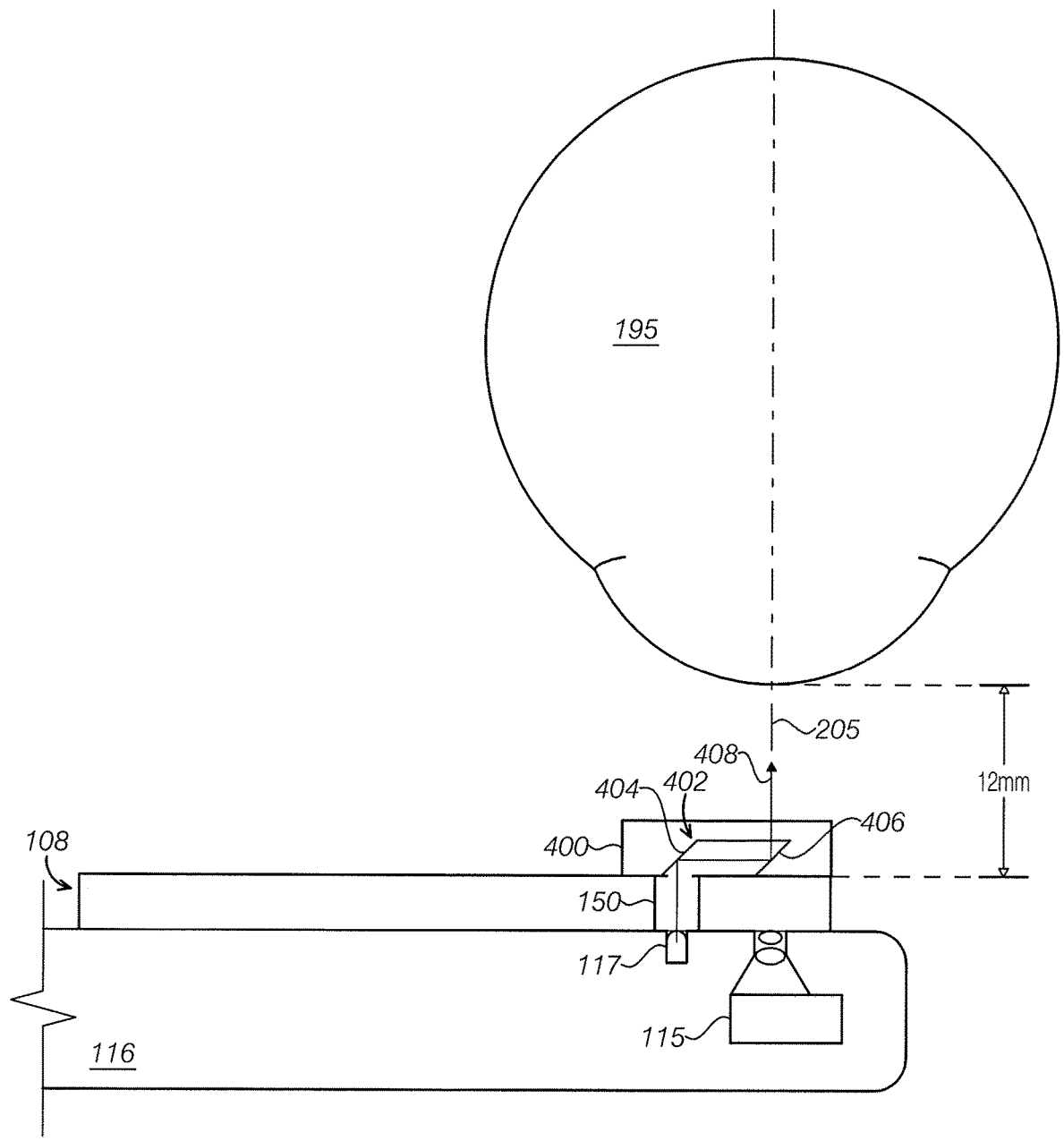
FIG. 19B is a schematic illustration of an adapter modifying a light path of a light source in accordance with some embodiments.
Figure 20:
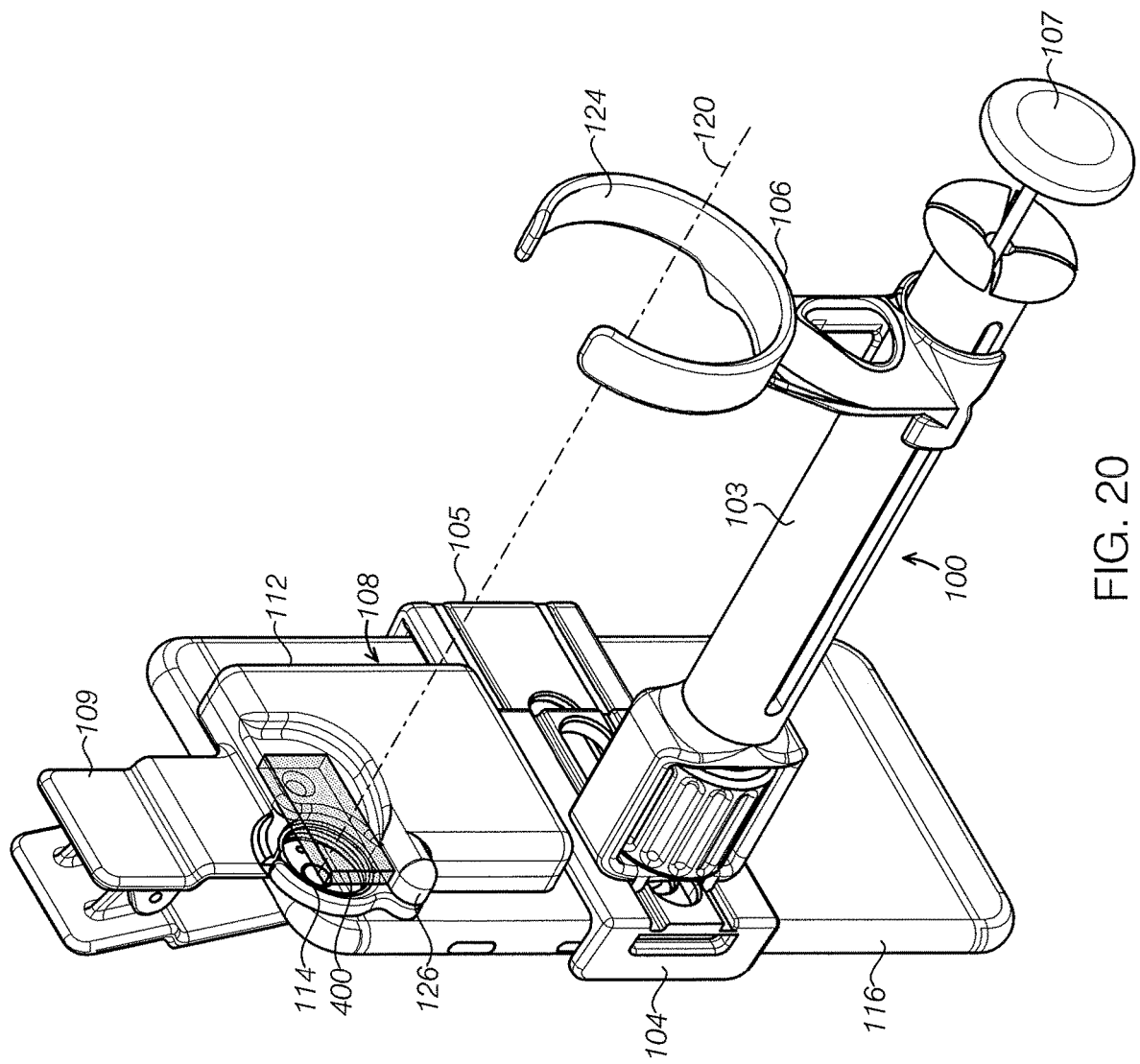
FIG. 20 is a schematic illustration of an adapter modifying a light path of a light source in combination with a modular adapter engaged with a smartphone in accordance with some embodiments.

FIGS. 19A-19B are schematic illustrations of a cross sectional view of an optical light guide 400 with an anterior adapter 108 and smartphone 116. FIG. 20 shows an isometric view of the optical light guide 400 with the anterior adapter 108 and smartphone 116. The illustrated optical light guide 400 includes a rhomboid prism 402. In other embodiments any of the mirror systems shown in the previous figures and described herein can be used. The rhomboid prism 402 includes a first surface 404 and a second surface 406 for directing light emitted from the light source 117 along an optical path 408. The first surface 404 directs light emitted from the light source 110 of the anterior adapter 108 along optical path 408 towards the second surface 406. The second surface 406 reflects the light reflected off of the first surface 404 along the optical path 408 towards the eye 195. The optical path 408 through the optical light guide 400 lines the optical path 408 exiting the optical light guide 400 to substantially coincide with the optical path 205 of the camera 115. In some embodiments the optical light guide 200 can line up the optical path 208 to substantially parallel but offset from the optical path 205 of the camera 115. The optical light guide 400 can move relative to the anterior adapter and optical axis 205 of the camera 115. For example the optical light guide 400 can move from a first position (shown in FIGS. 19A, 19B, and 20) with the optical path 408 in line with the optical path 205 of the camera 115 to a second position where the optical light guide 400 does not affect or overlap with the light source 110 or optical path 205 of the camera 115.

In some embodiments the adapter described herein can use the light source from the hand held computer device. For example, the anterior adapter can allow light from the hand held computer device to pass through the anterior adapter and travel along the path of the optical light guide. FIG. 19B illustrates an embodiment of the anterior adapter 108 that includes a light pass through or window 150. The pass through 150 allows the light source 117 from the smartphone 116 to pass through a portion of the anterior adapter 108 and go through the optical light guide 400 as shown in FIG. 19B. The illustrated optical light guide 400 includes a rhomboid prism 402. The rhomboid prism 402 includes a first surface 404 and a second surface 406 for directing light emitted from the light source 117 along an optical path 408. After the light passes through the window 150, the first surface 404 directs the light emitted from the light source 117 of the smartphone 116 along optical path 408 towards the second surface 406. The second surface 406 reflects the light reflected off of the first surface 404 along the optical path 408 towards the eye 195. The optical path 408 through the optical light guide 400 lines the optical path 408 exiting the optical light guide 400 to substantially coincide with the optical path 205 of the camera 115. In some embodiments the optical light guide 200 can line up the optical path 208 to substantially parallel but offset from the optical path 205 of the camera 115. The optical light guide 400 can move relative to the anterior adapter and optical axis 205 of the camera 115. For example the optical light guide 400 can move from a first position (shown in FIGS. 19A, 19B, and 20) with the optical path 408 in line with the optical path 205 of the camera 115 to a second position where the optical light guide 400 does not affect or overlap with the light source 117 or optical path 205 of the camera 115.

In some embodiments the telescoping arm can be permanently or reversibly mounted to the posterior mount or a case for the hand held device. In either case, the telescoping arm may be foldable such that the arm and lens mount distal to it are moved aside to allow the user to hold the mobile device closer to the patient's eye when using, for example, the anterior adapter. The telescoping arm may be attached to the case of the phone either through a two-point fixation undersized gripping mechanism as shown in the drawings, or through other mechanisms such as a depression within the case that fits the telescoping arm (female-male connectivity), a reversible locking fit wherein a button is pressed to release the arm from the case, a magnetic attachment mechanism, or a suction attachment mechanism.

In some embodiments the aperture of the LED light source could be adjustable to create varying diameters for the collimated beam. In some embodiments a collimating light element can be used in combination with the light source. Blue, red-free, and other types of lighting may be used, and infrared lighting may also be used. In addition, various filters could be used for the light source, for instance, to physically reduce the intensity of the light. This method could be used in place of the variable intensity light source, to provide one or more barrier-type filters for the light. Examples of such filters are neutral density filters and polarizing filters.

In some embodiments certain elements may be positioned in front of the camera lens to enhance image quality. Such elements include, for example, additional lenses that will serve to increase the magnification of the virtual image created by the ophthalmoscopy lens seen on the hand held computer device screen (e.g. to enable to occupy a greater percentage of the screen area) as well as filtering elements such as polarizing filters, neutral density filters, and pinhole filters that can reduce glare and light scatter.

In some embodiments the macro lens could include a rotating or sliding lens or filter set where the user can select from macro, blue filter, high magnification, and wide angle lenses by rotation the lens set in front of the lens of the hand held computer device.

In some embodiments the anterior adapter could further include an eye rest, e.g. a circular protrusion around the macro lens which could be place around the eye, to assist in positioning and stabilizing the anterior adapter and hand held computer device system and its various modular forms in front of the eye when using the anterior adapter to obtain an image of the eye.

In some embodiments the variable intensity external light source could be used with or without a mirror system or fiber optic element to guide the light.

In some embodiments an external fixation target could be added for the opposite eye that can be a blinking light or other form of adjustable fixation target. A moveable extension with a blinking light tip could be plugged into a phone audio jack or directly to the adapter itself (such as to the telescoping shaft or another part of either the anterior or posterior adapter) to direct a patient's gaze toward the light.

In some embodiments the LED light could be focused into an adjustable slit beam that can be directed through the cornea at an angle, mimicking the action of a traditional slit lamp. The LED light may also be set to a fixed intensity (without a variable intensity function).

In some embodiments the system could be enhanced to have a dedicated software application running on the hand held computer device to assist in image capture, light control, image analysis, image enhancement, data storage and data sharing as are common features of applications running on, for example, smartphones.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of imaging an anterior portion of a patient's eye, the method comprising:
    clamping an anterior adapter to a hand held computer device having a camera, the anterior adapter comprising: a variable intensity light source, a clamp configured to engage with the hand held computer device, and a movable macro lens configured to move the macro lens from a first position in coaxial alignment with an optical axis of the camera to a second position outside of the optical axis of the camera, the macro lens configured to image an anterior portion of the patient's eye;
    moving the macro lens to be in coaxial alignment with the optical axis of the camera of the hand held computer device;
    securing the macro lens in the first position by rotating the macro lens about a macro lens hinge of the anterior adapter and engaging the macro lens with a macro lens engagement surface of the anterior adapter, the macro lens engagement surface configured to secure the macro lens in the first position in coaxial alignment with the optical axis of the hand held computer device camera and prevent rotation of the macro lens about the macro lens hinge to a position outside of the first position;
    moving the hand held computer device and anterior adapter to focus on the anterior portion of the patient's eye; and
    receiving an image of the anterior portion of the patient's eye with the camera of the hand held computer device.

2. The method of claim 1, further comprising: adjusting the variable intensity light source to provide a desired level of light from the variable intensity light source to the anterior portion of the patient's eye.

3. The method of claim 1, further comprising: lining up the optical axis of the camera with an optical axis of the anterior adapter prior to clamping the anterior adapter.

4. The method of claim 1, wherein the hand held computer device is a smartphone, tablet, or other flatscreen computer device.

5. The method of claim 1, further comprising reversibly engaging the anterior adapter and the posterior adapter to form an interlocking connection between the anterior adapter and the posterior adapter.

6. The method of claim 1 further comprising:
    a light collimating element configured for use with the variable intensity light source wherein the light collimating element is moveable into a first position in an optical path of the variable intensity light source and a second position outside of the optical path of the variable intensity light source.

7. The method of claim 6 further comprising: positioning a lens or a mask in the optical path of the variable intensity light source when the collimating light source is moved into the first position.

8. The method of claim 1 further comprising filtering the light emitted by the variable intensity light source.

9. The method of claim 8 wherein after the filtering step the light is blue.

10. A method of imaging a posterior portion of a patient's eye, the method comprising:
   clamping an anterior adapter to the hand held computer device having the camera, the anterior adapter comprising: a variable intensity light source, a clamp configured to engage with the hand held computer device, and a movable macro lens configured to move the macro lens from a first position in coaxial alignment with an optical axis of the camera to a second position outside of the optical axis of the camera, the macro lens configured to image an anterior portion of the patient's eye;
   moving said macro lens to the second position outside the optical axis of the camera;
   securing a mount of a posterior adapter to a hand held computer device comprising a camera, the posterior adapter comprising a telescoping arm with a first end and a second end, the first end configured to removably engage with the mount and the second end configured to contact a lens mount configured to removably mount a posterior segment ophthalmoscopy lens configured for indirect ophthalmoscopy;
   adjusting the telescoping arm along an axis of the mount to coaxially line up the lens mount with an optical axis of the camera of the hand held computer device;
   engaging a lens configured for indirect ophthalmoscopy with the lens mount;
   moving a modular optical light guide relative to the anterior adapter to a position in line with an optical light path of the variable intensity light source;
   passing light from the variable-intensity light source through the modular optical light guide;
   moving the hand held computer device and the posterior adapter to focus on the posterior portion of the patient's eye;
   adjusting a length of the telescoping arm to focus the camera of the hand held computer device on an image of the posterior portion of the patient's eye in the lens configured for indirect ophthalmoscopy; and
   receiving an image of the posterior portion of the patient's eye with the camera of the hand held computer device, wherein,
   the modular optical light guide further comprising a rhomboid prism with a first surface and a second surface and further comprising reflecting light from the variable intensity light source off of the first surface towards the second surface and reflecting light from the first surface off of the second surface to be substantially parallel to the optical pathway of the hand held computer device camera or to substantially coincide with the optical pathway of the hand held computer device camera.

11. The method of claim 10, further comprising securing the mount of the posterior adapter by adjusting a length of the axis of the mount to accommodate a dimension of the hand held computer device.

12. The method of claim 11, further comprising engaging a first hand held computer device contact surface and a second hand held computer device contact surface of the mount with the hand held computer device.

13. The method of claim 11, further comprising: locking a length of the axis of the mount to secure the mount relative to the hand held computer device.

14. The method of claim 13, further comprising locking a position of the telescoping arm along the axis of the mount after adjusting the telescoping arm along the axis of the mount to coaxially line up the lens mount with the optical axis of the camera of the hand held computer device.

15. The method of claim 10, further comprising: adjusting the variable intensity light source to provide a desired level of light to the posterior portion of the patient's eye.

16. The method of claim 10, further comprising adjusting the variable intensity light source to provide a desired level of light to the anterior portion of the patient's eye.

17. The method of claim 16, further comprising:
   moving the macro lens to be in coaxial alignment with the optical axis of the camera of the hand held computer device;
   moving the hand held computer device and anterior adapter to focus on the anterior portion of the patient's eye; and
   taking an image of the anterior portion of the patient's eye with the camera of the hand held computer device.

18. The method of claim 10, further comprising passing light from the variable intensity light source through a light collimating element to provide collimated light to the anterior portion or the posterior portion the patient's eye.

19. The method of claim 10, further comprising obtaining a direct ophthalmoscopy image of the patient's eye using the modular optical light guide for direct ophthalmoscopy with the anterior adapter.

20. The method of any of claim 10, wherein the hand held computer device is a smartphone, tablet, or other flatscreen computer device.

21. The method of any of claim 10, further comprising reversibly engaging the anterior adapter and the posterior adapter to form an interlocking connection between the anterior adapter and the posterior adapter.

22. The method of claim 10, further comprising:
   powering the variable intensity light source using a removeable battery source.

23. The method of claim 10 further comprising:
   engaging a patient engagement surface adjacent the lens mount to a portion of a face of the patient.

* * * * *